(12) United States Patent
Zhang et al.

(10) Patent No.: US 10,883,957 B2
(45) Date of Patent: *Jan. 5, 2021

(54) MAGNESIUM SENSING MEMBRANE FOR POTENTIOMETRIC ION SELECTIVE ELECTRODE FOR MEASURING IONIZED MAGNESIUM AND METHODS OF PRODUCTION AND USE THEREOF

(71) Applicant: Siemens Healthcare Diagnostics Inc., Tarrytown, NY (US)

(72) Inventors: Wei Zhang, Needham, MA (US); Kevin Horan, Raynham, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/782,511

(22) Filed: Feb. 5, 2020

(65) Prior Publication Data

US 2020/0173955 A1 Jun. 4, 2020

Related U.S. Application Data

(63) Continuation of application No. 16/297,811, filed on Mar. 11, 2019, now Pat. No. 10,605,762, which is a continuation of application No. 15/934,294, filed on Mar. 23, 2018, now Pat. No. 10,241,071, which is a continuation of application No. 15/303,843, filed as
(Continued)

(51) Int. Cl.
*G01N 27/333* (2006.01)
*G01N 33/487* (2006.01)
*G01N 27/416* (2006.01)

(52) U.S. Cl.
CPC ....... *G01N 27/3335* (2013.01); *G01N 27/333* (2013.01); *G01N 27/4163* (2013.01); *G01N 33/48707* (2013.01); *G01N 33/487* (2013.01)

(58) Field of Classification Search
None
See application file for complete search history.

(56) References Cited

U.S. PATENT DOCUMENTS

| | | |
|---|---|---|
| 5,667,983 A | 9/1997 | Abel et al. |
| 8,496,800 B2 | 7/2013 | Zhang et al. |
| 9,952,174 B2 * | 4/2018 | Zhang ................ G01N 27/333 |

FOREIGN PATENT DOCUMENTS

| | | |
|---|---|---|
| JP | H06288962 A | 10/1994 |
| WO | 8700286 A1 | 1/1987 |
| WO | 2010021923 A1 | 2/2010 |

(Continued)

OTHER PUBLICATIONS

Rouilly et al., "Neutral Ionophore-Based Selective Electrode for Assaying the Activity of Magnesium in Undiluted Blood Serum," Clin. Chem. 36/3, 466-469 (1990).
(Continued)

*Primary Examiner* — Alexander S Noguerola
(74) *Attorney, Agent, or Firm* — Dunlap Codding P.C.

(57) ABSTRACT

A magnesium sensing membrane is disclosed for use in a potentiometric ion selective electrode that exhibits improved stability upon exposure to surfactant-containing reagents. Kits containing same are disclosed, along with methods of production and use of the magnesium sensing membrane.

14 Claims, 15 Drawing Sheets

Related U.S. Application Data application No. PCT/US2015/025680 on Apr. 14, 2015, now Pat. No. 9,952,174.

(60) Provisional application No. 61/981,277, filed on Apr. 18, 2014.

(56) References Cited

FOREIGN PATENT DOCUMENTS

| WO | WO-2010021923 A1 * | 2/2010 | ........... G01N 27/333 |
|---|---|---|---|
| WO | 2010076717 A1 | 7/2010 | |

OTHER PUBLICATIONS

Buhlmann et al., "Carrier-Based Ion-Selective Electrodes and Bulk Optodes. 2. Ionophores for Potentiometric and Optical Sensors", Chem. Rev. 1998, 98, 1593-1687.
Oesch et al., "Design of Neutral Hydrogen Ion Carriers for Solvent Polymeric Membrane Electrodes of Selected pH Range," Anal. Chem. 1986, 58, 2285-2289.
Zhang et al, "Development of Magnesium-Ion-Selective Microelectrodes Based on a New Neutral Carrier ETH 5504," Electroanalysis 1998, 10, No. 17, pp. 1174-1181.
Wu et al., "Determination of Magnesium and Calcium in Biological Samples by Potentiometric Stripping Analysis", 2010, J. Chin. Chem. Soc. 57(4A): pp. 647-652.
Maj-Zurawska et al., "Fully automated potentiometric determination of ionized magnesium in blood serum", Sep. 1990, Analytica Chimica Acta 236(2), pp. 331-335.
Marsoner et al., "Measurement of ionized magnesium with neutral carrier based ISE's. Progress and results with the AVL 988-4 magnesium analyzer", 1994, Scandinavian Journal of Clinical and Laboratory Investigation, vol. 54, 1994—Issue sup217, pp. 45-51.
Mikhelson et al., "Potentiometric Performance and Interfacial Kinetics of Neutral Ionophore Based ISE Membranes in Interfering Ion Solutions Before and After Contact with Primary Ions", 2001, Electroanalysis 13(10), pp. 876-881.
European Search Report and Written Opinion of European Application No. EP 15779345.6 dated Jan. 11, 2017.
Spichiger et al., "Critical parameters and optimization of a magnesium-selective liquid membrane electrode for application to human blood serum", Jan. 1, 1991, Fresenius' Journal of Analytical Chemistry, vol. 341; No. 12; pp. 727-731.
Zhang et al., "An impedance study of Mg<2+>-selective membranes", Mar. 1, 2000, Electrochimica Acta, Elsevier Science Publishers, Barking, GB, vol. 45, No. 14, pp. 2259-2266.
International Search Report and Written Opinion of International Application No. PCT/US2015/025680 dated Jul. 9, 2015.
Spichiger, "History of the development of magnesium-selective ionophores and magnesium-selective electrodes", 1993, Electroanalysis, vol. 5, pp. 739-745.
Eugster et al., "Characterization procedure for ion-selective electrode assays of magnesium activity in aqueous solutions of physiological composition", May 1993, Clin Chem.; 39(5): pp. 855-859.
O'Donnell et al., "Development of magnesium-selective ionophores", 1993, Analytica Chimica Acta. 281(1): pp. 129-134.
Espadas-Torre et al.,"Thrombogenic Properties of Untreated and Poly(ethylene oxide)-Modified Polymeric Matrices Useful for Preparing Intraarterial Ion-Selective Electrodes", Sep. 15, 1995, Anal. Chem., vol. 67, No. 18, pp. 3108-3114.
Malinowska et al., "Influence of nonionic surfactants on the potentiometric response of ion-selective polymeric membrane electrodes designed for blood electrolyte measurements", Apr. 15, 1998, Anal Chem.;70(8): pp. 1477-1488.
Zhang et al. "A Comparison of Neutral Mg2+Selective Ionophores in Solvent Polymeric Membranes: Complex Stoichiometry and Lipophilicity", Jan. 2000, Analytical Sciences 16(1): pp. 11-18.
Scharbert et al., "Effect of pH levels on platelet aggregation and coagulation: a whole blood in vitro study", 2011, Critical Care vol. 15, Suppl 1: P446; p. S157.
Lim et al., "Protein adsorption to planar electrochemical sensors and sensor materials", 2004, Pure Appl. Chem., vol. 76, No. 4, pp. 753-764.
Rayana et al., "Guidelines for sampling, measuring and reporting ionized magnesium in undiluted serum, plasma or blood", 2005, Clin Chem Lab Med.; 43(5): pp. 564-569.
Karlsen, "The Effect of Non-Ionic Surfactants on the Potentiometric Response of Ion Selective Electrodes", Jun. 9, 2009, pp. 1-141.
Vladkova, "Surface Engineering of Blood Contacting Polymeric Biomaterials", 2013, Surface Engineering of Polymeric Biomaterials—Chapter 4, pp. 231-294.
Gunzel et al., "Determination of [Mg.sup.2+]an update on the use of Mg.sup.2+ -selective electrodes", 2002, BioMetals 15: pp. 237-249.
Malinowska et al., "Potentiometric Response of Magnesium-selective Membrane Electrode in the Presence of Nonionic Surfactants", 1999, Analytica Chimica Acta 382(3): pp. 265-275.
Zhang, "Point of Care Testing of Ionized Magnesium in Blood with Potentiometric Sensors—Opportunities and Challenges", 2011, American Journal of Biomedical Sciences, 3(4): pp. 301-312.
European Search Report and Written Opinion of European Application No. EP 18158118.2 dated Jun. 11, 2018.
Intention to Grant of European Application No. EP 18158118.2 dated May 23, 2019.

* cited by examiner

MAGNESIUM SENSING MEMBRANE FOR POTENTIOMETRIC ION SELECTIVE ELECTRODE FOR MEASURING IONIZED MAGNESIUM AND METHODS OF PRODUCTION AND USE THEREOF

CROSS REFERENCE TO RELATED APPLICATIONS/INCORPORATION BY REFERENCE STATEMENT

The subject application is a continuation of U.S. Ser. No. 16/297,811, filed Mar. 11, 2019; which is a continuation of U.S. Ser. No. 15/934,294, filed Mar. 23, 2018, now U.S. Pat. No. 10,241,071, issued Mar. 26, 2019; which is a continuation of U.S. Ser. No. 15/303,843, filed Oct. 13, 2016, now U.S. Pat. No. 9,952,174, issued Apr. 24, 2018; which claims benefit of US National Stage of International Application No. PCT/US2015/025680 filed Apr. 14, 2015 and claims priority to U.S. provisional Application No. 61/981,277, filed Apr. 18, 2014. The entire contents of each of the above-referenced patents and patent applications are hereby expressly incorporated herein by reference.

STATEMENT REGARDING FEDERALLY FUNDED RESEARCH OR DEVELOPMENT

Not Applicable.

BACKGROUND

The use of ion selective electrodes (ISEs) to determine the presence and quantity of various analytes in biological samples has become a useful diagnostic technique. Indeed, ISEs have been used to detect analytes such as magnesium, sodium, potassium, calcium, and chloride, among others. Some of these ISEs are often housed within clinical diagnostic instruments for simultaneous analysis of a large number of analytes.

Surfactants are often included in reagents used during the operation of ISEs. Various surfactants may be used for this purpose; however, the utility of the surfactant is highly dependent upon the sensing membrane of the ISE. For example, an unsuitable surfactant can result in a shift in electromotive force (EMF) bias that does not allow the electrode to measure a biologically relevant amount of an analyte.

It has been known that the concentration of lipophilic borate salt present in a sensing membrane plays an important role in a potentiometric selective electrode, especially for a magnesium ion ($Mg^{2+}$) selective electrode. The level of borate present in the sensing membrane modulates the selectivity coefficient of $Mg^{2+}$ over interfering cations such as $Ca^{2+}$, $Na^+$, and $K^+$, based on cation charge number, complex stoichiometry with the neutral ionophore, and response kinetics. For the $Mg^{2+}$ ISE, a borate-to-ionophore mol ratio of 155 mol % has been regarded as the optimized formulation that provides the best selectivity pattern.

As for the responding mechanism of the Mg-ISE, there are at least four competitive interactions that have been identified that interfere with the $Mg^{2+}$ and ionophore (ETH5506) primary interaction at the membrane-sample interface for blood $Mg^{2+}$ ISE's. These four competitive interactions are outlined below, and the causes of the interactions, as well as the various prior art attempts to overcome them, are discussed in detail herein below.

Primary mechanism (PM): ETH5506 (memb)+$Mg^{2+}$ (aq)
Competitive mechanism-1 (CM-1): ETH5506 (memb)+$Ca^{2+}$ (aq)
Competitive mechanism-2 (CM-2): Ion-exchange by lipophilic borate (memb, interface)
Competitive mechanism-3 (CM-3): Ion-exchange by adsorbed blood protein layer (interface)
Competitive mechanism-4 (CM-4): Ion-exchange by surfactant adsorption layer (interface)

PM and CM-1: Among these mechanisms, the primary mechanism (PM) can be differentiated from the competitive mechanism CM-1 by adjusting the borate:ionophore ratio. Stoichiometry of the $Mg^{2+}$-ETH5506 ISE is 1:1 and that for $Ca^{2+}$-ETH5506 ISE is 1:2. The lipophilic borate anion sites in the PVC membrane help stabilize the $Mg^{2+}$-ETH5506 ISE and $Ca^{2+}$-ETH5506 ISE to different extents with an electrical balance across the membrane-sample phase boundary (charge-transfer process). An optimal borate:ETH5506 mol ratio of 150 mol % has been calculated and experimentally verified (O'Donnell et al., Anal. Chim. Acta (1993) 281:129), at which the Mg-ISE gains the lowest log $K^{pot}_{Mg,Ca}$ (−2) with workable selectivities against $Na^+$ and $K^+$ (log $K^{pot}_{Mg,Na}$ (−4) and log $K^{pot}_{Mg,K}$ (−3)).

PM and CM-2: When the borate:ETH5506 mol ratio is reduced, the Mg-ISE favors to respond to $Ca^{2+}$. At a borate:ETH5506 ratio of 50 mol %, the Mg-ISE tends to have equal sensitivity to $Ca^{2+}$ and $Mg^{2+}$ because of the different stoichiometries of $Mg^{2+}$ and $Ca^{2+}$ with ETH5506. When more borate is added (to a ratio of >150 mol %), the second competitive mechanism (CM-2) is seen, where the Mg-ISE tends to become an ion-exchange membrane dominated by the lipophilic borate in the membrane. The membrane's response follows Hofmeister's series. Monovalent cations are favored more than divalent cations. In addition, more $Na^+$ and $K^+$ interference can be expected.

PM and CM-3: Many studies have shown that blood samples tend to coagulate and aggregate on the surface of the PVC membrane, forming thin coating layers of platelet, fibrinogen, IgG, and albumin (Espadas-Torre et al., Anal. Chem. (1995) 7:3108-3114; Lim et al., Pure Appl. Chem. (2004) 76:753-764; and Surface Engineering of Blood Contacting Polymeric Biomaterials, p. 231). In the competitive mechanism CM-3, the ion-exchange properties of such a layer compete with the primary interaction (PM). This blood coating layer is sensitive to the pH (Scharbert, et al., Crit. Care (2011) 15:446) and surfactant levels of the various reagents (calibrators, wash, and QCs) utilized with the ISE. Variation of the pH may change the layer formation, and thus the ion-exchange mechanism can be affected. To prevent the competitive mechanism CM-3 from occurring on the Mg-ISE membrane, several approaches have been investigated, including using alternative polymeric materials, anti-protein adsorption coating layers, LbL, etc.

PM and CM-4: In automatic blood analyzers, surfactants are present in calibrating, rinse, and quality control solutions. Many studies have demonstrated the impact of surfactant on potentiometric sensors, especially on neutral ionophore-based $Mg^{2+}$ selective electrodes (Malinowska et al., Anal. Chim. Acta (1999) 382:265-275). Surfactants containing poly(ethylene oxide) derivatives, which are widely used in automatic clinical analyzers, have shown severe impact on response performance of $Mg^{2+}$ selective electrodes, including effects to response kinetics, slope, and selectivity. The mechanism of such interference is explained by the partitioning of nonionic surfactant into the membrane phase and the concomitant enhanced extraction of cations present in the sample phase. The partitioning process of the surfactant can significantly change the selectivity pattern and response kinetics of the membrane, which can be a function of the partitioning coefficients of the surfactant into the polymer membrane, the relative binding coefficients of primary and interfering ions with the surfactant and the ionophore, respectively, and/or the concentration of the surfactant that is present in the sequence of sample/calibrating/rinse solutions in the sensing system of the automatic analyzers. Moreover, the extent of the effect of the surfactant depends on the ratio of the stability constants of complexes formed with interfering cations by the surfactant and ionophore, respectively. The stronger the complexation of interfering cation with the surfactant, and the weaker the interaction of the primary ion with the ionophore within the membrane, a greater change in the potentiometric ion selectivity can be expected. However, the impact of the surfactant can be significantly reduced by using different kinds of surfactant with low HLB (hydrophile-lipophile balance), such as MEGA-8 and MEGA-9 surfactants.

Lipophilic borate has been known to interact with poly (ethylene oxide)-containing surfactants to form a complex. In neutral ionophore-based cation selective electrodes, the presence of lipophilic borate in the polymer membrane can enhance partitioning of surfactant and change the response performance of ISEs.

Therefore, new and improved magnesium sensing membrane compositions for potentiometric ion selective electrodes that overcome the disadvantages of the prior art are desired. It is to such membranes, as well as compositions, kits, devices, and methods related thereto, that the presently disclosed and claimed inventive concept(s) is directed.

DESCRIPTION OF THE SEVERAL VIEWS OF THE DRAWINGS

FIG. 1A illustrates the responses observed upon exposure to Series Aa, Ab, and Ac (0.0 g/L, 0.5 g/L, and 0.1 g/L, respectively, Brij surfactant in a simple $MgCl_2$ solution), while FIG. 1B illustrates the responses observed upon exposure to Series Ba, Bb, and Bc (0.0 g/L, 0.5 g/L, and 0.1 g/L, respectively, Brij surfactant in an electrolyte background solution).

DETAILED DESCRIPTION

Figure 1A:
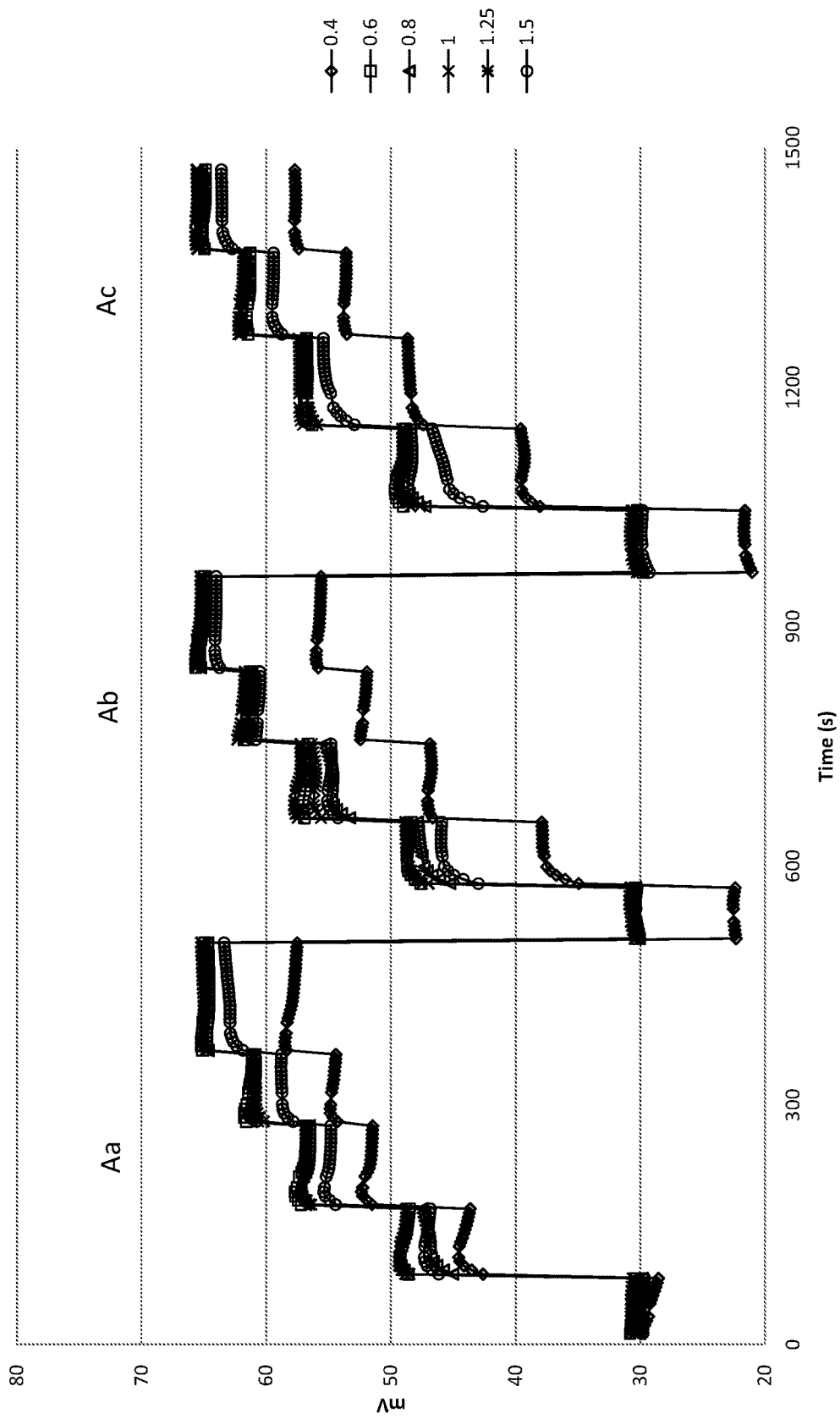
FIGS. 1A and 1B graphically illustrate the raw responses of six different magnesium sensors, each of which contains a different borate:ETH5506 ratio (40 mol % (0.4), 60 mol % (0.6), 80 mol % (0.8), 100 mol % (1.0), 125 mol % (1.25), and 150 mol % (1.5) ratios) upon exposure to different surfactant-containing solutions.

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well known and commonly used in the art.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and/or methods disclosed and claimed herein can be made and executed without undue experimentation in light of the present disclosure. While the compositions and methods of this presently disclosed and claimed inventive concept(s) have been described in terms of preferred embodiments, it will be apparent to those of skill in the art that variations may be applied to the compositions and/or methods and in the steps or in the sequence of steps of the method described herein without departing from the concept, spirit and scope of the presently disclosed and claimed inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The singular forms "a," "an," and "the" include plural referents unless the context clearly indicates otherwise. Thus, for example, reference to "a compound" may refer to 1 or more, 2 or more, 3 or more, 4 or more or greater numbers of compounds. The term "plurality" refers to "two or more." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by ±20% or ±10%, or ±5%, or ±1%, or ±0.1% from the specified value, as such variations are appropriate to perform the disclosed methods and as understood by persons having ordinary skill in the art. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in this specification and claim(s), the terms "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, the phrase "associated with" includes both direct association of two moieties to one another as well as indirect association of two moieties to one another. Non-limiting examples of associations include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety.

The term "purified" as used herein means at least one order of magnitude of purification is achieved compared to the starting material or of the natural material, for example but not by way of limitation, two, three, four or five orders of magnitude of purification of the starting material or of the natural material. Thus, the term "purified" as utilized herein does not necessarily mean that the material is 100% purified, and therefore such term does not exclude the presence of other material(s) present in the purified composition.

The terms "analog" and "derivative" are used herein interchangeably and refer to a substance which comprises the same basic carbon skeleton and carbon functionality in its structure as a given compound, but can also contain one or more substitutions thereto. The term "substitution" as used herein will be understood to refer to the replacement of at least one substituent on a compound with a residue R. In certain non-limiting embodiments, R may include H, hydroxyl, thiol, a halogenid selected from fluoride, chloride bromide or iodite, a C1-C4 compound selected one of the following: linear, branched or cyclic alkyl, optionally substituted, and linear branched or cyclic alkenyl, wherein the optional substitutents are selected from one or more alkenylalkyl, alkynylalkyl, cycloalkyl, cycloalkenylalkyl, arylalkyl, heteroarylalkyl, heterocyclealkyl, optionally substituted heterocycloalkenylalkyl, arylcycloalkyl, and arylheterocycloalkyl, each of which is optionally substituted wherein the optional substitutents are selected from one or more of alkenylalkyl, alkynylalkyl, cycloalkyl, cyclalkenylalkyl, arylalkyl, alkylaryl, heteroarylalkyl, heterocyclealkyl, optionally substituted heterocycloalkenylalkyl, arylcycloalkyl, and arylheterocyclalkyl, phenyl, cyano, hydroxyl, alkyl, aryl, cycloalkyl, cyano, alkoxy, alkylthio, amino, —NH (alkyl), —NH(cycloalkyl)2, carboxy and —C(O))-alkyl.

The term "sample" as used herein will be understood to include any type of biological sample that may be utilized in accordance with the presently disclosed and claimed inventive concept(s). Examples of biological samples that may be utilized include, but are not limited to, whole blood or any portion thereof (i.e., plasma or serum), saliva, sputum, cerebrospinal fluid (CSF), skin, interstitial fluid, tears, mucus, urine, swabs, combinations, and the like.

Turning now to the presently disclosed and claimed inventive concept(s), a new and improved magnesium sensing membrane is provided that exhibits improved stability over existing magnesium sensing membranes upon exposure to surfactant-containing reagents. The new magnesium sensing membrane can be used in the development of new potentiometric ion selective electrodes adaptable for central laboratory and/or POC use.

Certain embodiments of the presently disclosed and claimed inventive concept(s) are directed to a magnesium sensing membrane for a potentiometric ion selective electrode that detects ionized magnesium in a biological sample. The magnesium sensing membrane may be a conventional membrane or a solid-state, planar membrane. The magnesium sensing membrane includes an ionophore having a tripodal stereochemical structure, a lipophilic borate salt, and a polymer matrix in which the ionophore and lipophilic borate salt are disposed. The polymer matrix includes a polymer and a plasticizer.

The lipophilic borate salt is present in an amount that provides a mol ratio of lipophilic borate salt to ionophore in a range of from about 60 mol % to about 100 mol %. Non-limiting examples of borate:ionophore ratios that may be utilized include about 60 mol %, about 65 mol %, about 70 mol %, about 75 mol %, about 80 mol %, about 85 mol %, about 90 mol %, about 95 mol %, and about 100 mol %. A particular non-limiting example of a borate:ionophore ratio is about 75 mol %.

Any ionophore having a tripodal stereochemical structure that is known or otherwise contemplated within the art and is capable of functioning in accordance with the present disclosure falls within the scope of the presently disclosed and claimed inventive concept(s). In one embodiment, the ionophore may have at least one malonic imide functional group. Non-limiting examples of ionophores that may be utilized in accordance with the presently disclosed and claimed inventive concept(s) include ionophores represented by any of the structures of Formulas I-IV:

Formula I

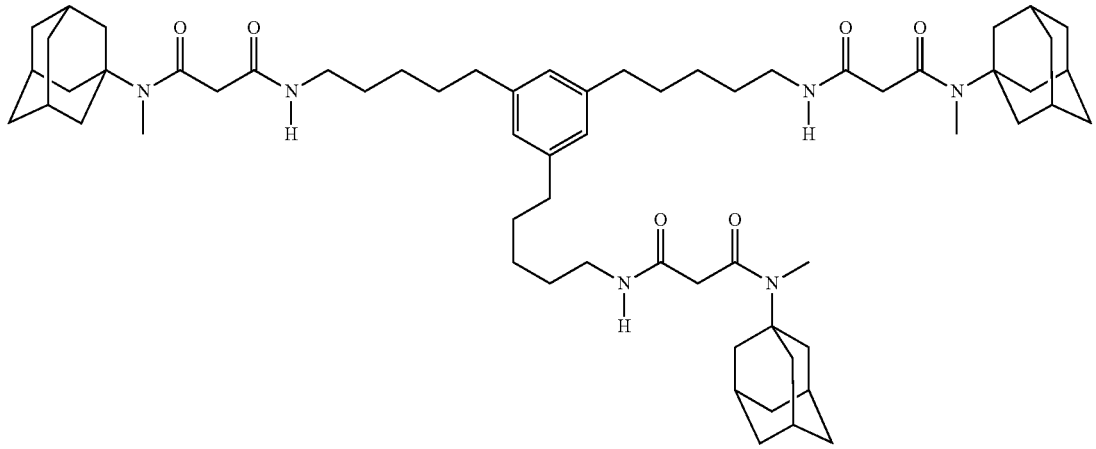

Formula II

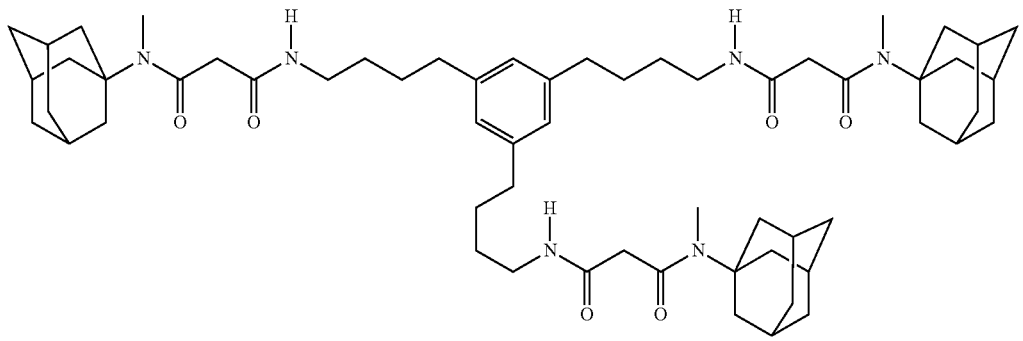

Formula III

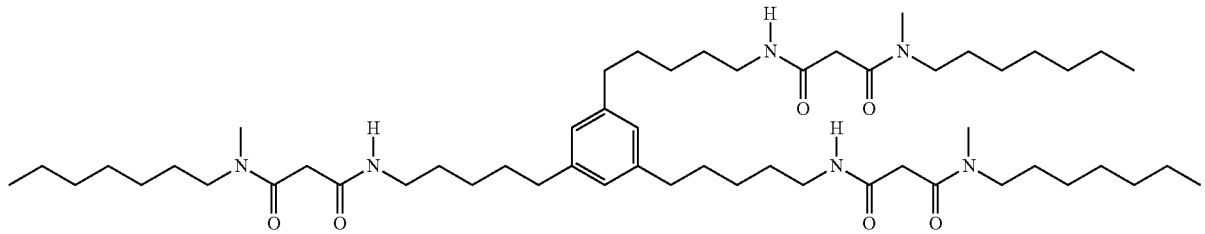

Formula IV

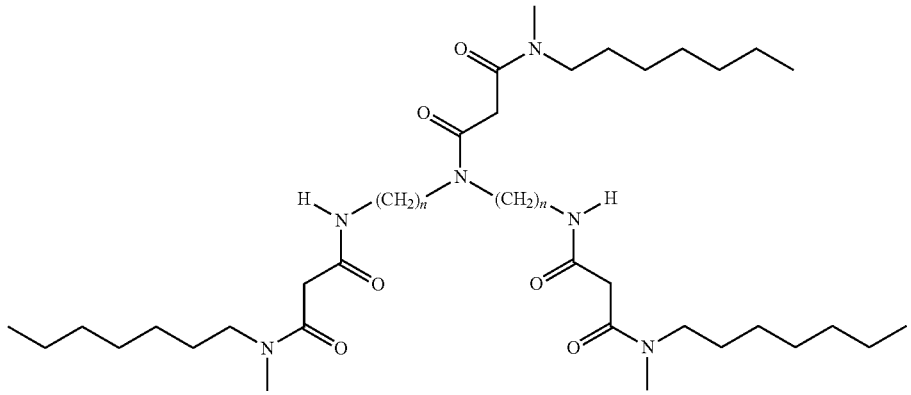

In Formula IV, n is in the range of from about 6 to about 8. The ionophores represented by any of the structures of Formulas I-III are known in the art by the product designations ETH5506, ETH5504, ETH3832, respectively. When n is 6 in Formula IV, the ionophore is known by the product designation ETH5282; when n is 8 in Formula IV, the ionophore is known by the product designation ETH7025. "ETH" denotes the German version of the Swiss Federal Institute of Technology (Eidgenösissche Technische Hochschule).

Any lipophilic borate salt known or otherwise contemplated within the art and capable of functioning as described herein may be utilized in accordance with the presently disclosed and claimed inventive concept(s). Non-limiting examples of lipophilic borate salts that may be utilized herein include the following:

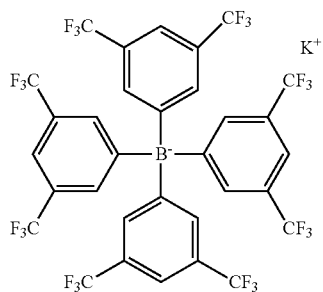

Potassium tetrakis[3,5-bis(trifluoromethyl)phenyl]borate or
Sodium tetrakis[3,5-bis(trifluoromethyl)phenyl]borate; and

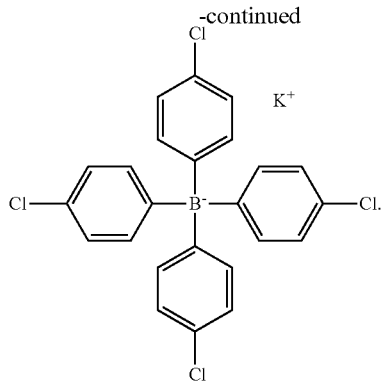

Potassium tetrakis(4-chlorophenyl)borate

Any polymer known or otherwise contemplated within the art and capable of functioning as described herein may be utilized as part of the polymer matrix, in accordance with the presently disclosed and claimed inventive concept(s). Non-limiting examples of polymers that may be utilized herein include poly(vinyl chloride), polyurethane, and combinations thereof.

Any plasticizer known or otherwise contemplated within the art and capable of functioning as described herein may be utilized as part of the polymer matrix, in accordance with the presently disclosed and claimed inventive concept(s). Non-limiting examples of plasticizers that may be utilized herein include the following:

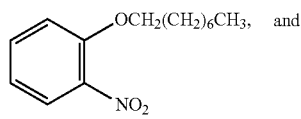

2-Nitrophenyl octyl ether

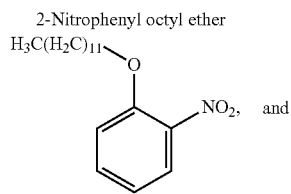

2-Nitrophenyl dodecyl ether

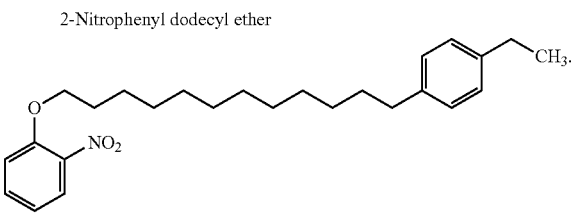

[12-(4-Ethylphenyl)dodecyl] 2-nitrophenyl ether

Another embodiment of the presently disclosed and claimed inventive concept(s) is directed to a potentiometric ion selective electrode that detects ionized magnesium in a biological sample. The potentiometric ion selective electrode comprises any of the magnesium sensing membranes described or otherwise contemplated herein above.

Another embodiment of the presently disclosed and claimed inventive concept(s) is directed to a method of measuring a level of magnesium ion present in a biological sample. In the method, any of the potentiometric ion selective electrodes described or otherwise contemplated is contacted with a biological sample, and a level of magnesium ion present in the biological sample is measured using the potentiometric ion selective electrode.

The method may further include the step of contacting the potentiometric ion selective electrode with a reagent comprising a poly(ethylene oxide) surfactant. The poly(ethylene oxide) surfactant may be utilized at any concentration that allows the surfactant and the potentiometric ion selective electrode to function in accordance with the presently disclosed and claimed inventive concept(s). A non-limiting example of a poly(ethylene oxide) surfactant concentration that falls within the scope of the presently disclosed and claimed inventive concept(s) is less than about 100 mg/L.

Any poly(ethylene oxide) surfactants known or otherwise contemplated within the art and capable of functioning as described herein may be utilized in accordance with the presently disclosed and claimed inventive concept(s). Non-limiting examples of poly(ethylene oxide) surfactants that may be utilized in accordance with the presently disclosed and claimed inventive concept(s) are represented by the structures of Formulas V-VII.

Formula V

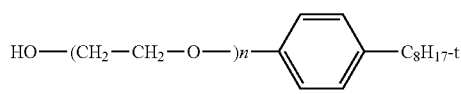

Formula VI

Formula VII

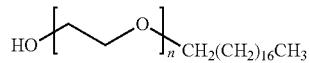

In Formula V, n is in the range of from about 9 to about 10; in Formula VII, n is about 100. One non-limiting example of a surfactant represented by the structure of Formula V (for example, t-octylphenoxypolyethoxyethanol) is sold under the trade name TRITON™ X-100 (Sigma-Aldrich, St. Louis, Mo.). One non-limiting example of a surfactant represented by the structure of Formula VI (for example, polyoxyethylene 23 lauryl ether) is known in the art by the product designation Brij-35. A non-limiting example of a surfactant represented by the structure of Formula VII (wherein n is about 100) is polyoxyethylene(100) stearyl ether nonionic surfactant, which is known in the art by the product designation Brij-700 (CAS No. 9005-00-9). Particular non-limiting examples of the surfactants represented by the structure of Formula VII are disclosed in U.S. Pat. No. 8,496,900, issued to Zhang et al. on Jul. 30, 2013.

Yet another embodiment of the presently disclosed and claimed inventive concept(s) includes a kit containing any of the membrane(s) and/or reagents described or otherwise contemplated herein. For example but not by way of limitation, a kit may include any of the magnesium sensing membranes described herein or any of the potentiometric ion selective electrodes containing said membrane. In addition, the kit may further include one or more reagents that comprise a poly(ethylene oxide) surfactant described or otherwise contemplated herein. The reagent(s) may be one or more calibration reagents, one or more wash reagents, or one or more quality control reagents, or any combination of the above.

In addition, the kit may further contain other reagent(s) for conducting any of the particular methods described or otherwise contemplated herein. The nature of these additional reagent(s) will depend upon the particular assay format, and identification thereof is well within the skill of one of ordinary skill in the art.

The components/reagents may each be disposed in separate containers/compartments of the kit, or various components/reagents can be combined in one or more containers/compartments of the kit, depending on the competitive nature of the components/reagents and/or the stability of the components/reagents. The kit can further include other separately packaged reagents for conducting an assay. The relative amounts of the various components/reagents in the kits can vary widely to provide for concentrations of the components/reagents that substantially optimize the reactions that need to occur during the assay methods and further to optimize substantially the stability/sensitivity of an assay. Positive and/or negative controls may be included with the kit. The kit can further include a set of written instructions explaining how to use the kit. For example but not by way of limitation, the kit may further include instructions for rinsing, calibrating, and/or operating the potentiometric ion selective electrode. A kit of this nature can be used in any of the methods described or otherwise contemplated herein.

EXAMPLE

An Example is provided hereinbelow. However, the presently disclosed and claimed inventive concept(s) is to be understood to not be limited in its application to the specific experimentation, results, and laboratory procedures disclosed herein below. Rather, the Example is simply provided as one of various embodiments and are meant to be exemplary, not exhaustive.

Materials and Methods

Reagents: A reagent matrix was designed to test: (1) the electrolyte background effect of the Brij700 surfactant on the Mg-ISE (wherein the surfactant is present in simple $Mg^{2+}$ solutions and in background electrolyte solutions containing $Na^+$ and $Ca^{2+}$); and (2) different levels of the Brij700 surfactant in simple solutions (0, 0.05, 0.10 g/L). The Solution series Aa to Ac tested the impact of the Brij surfactant on the Mg-ISE in simple $Mg^{2+}$ solutions, while the Solution series Ba to Bc tested the impact of the Brij surfactant on the Mg-ISE in a fixed electrolyte background.

Membranes: Six Mg-ISE membranes were made with varying borate to ETH5506 mol %: 40 mol %; 60 mol %; 80 mol %; 100 mol %; 125 mol %; and 150 mol %. The total membrane weight was targeted at 400 mg with 2 wt % ETH5506. The membranes were prepared following the conventional preparation method. The internal electrolyte solution in Philips Body electrodes was 1 mM $MgCl_2$; 1.0 mM $CaCl_2$; 150 mM NaCl; pH 7.4.

Measurements: Mg-ISE electrodes were conditioned for 24 hours before measurement. Saturated Ag/AgCl electrode was used as reference electrode. EMF16 was used for data acquisition. After contact with the solutions with Brij (Ac), the electrodes were intensively rinsed using no Brij solution (Ba).

Results and Discussion

Figure 1B:
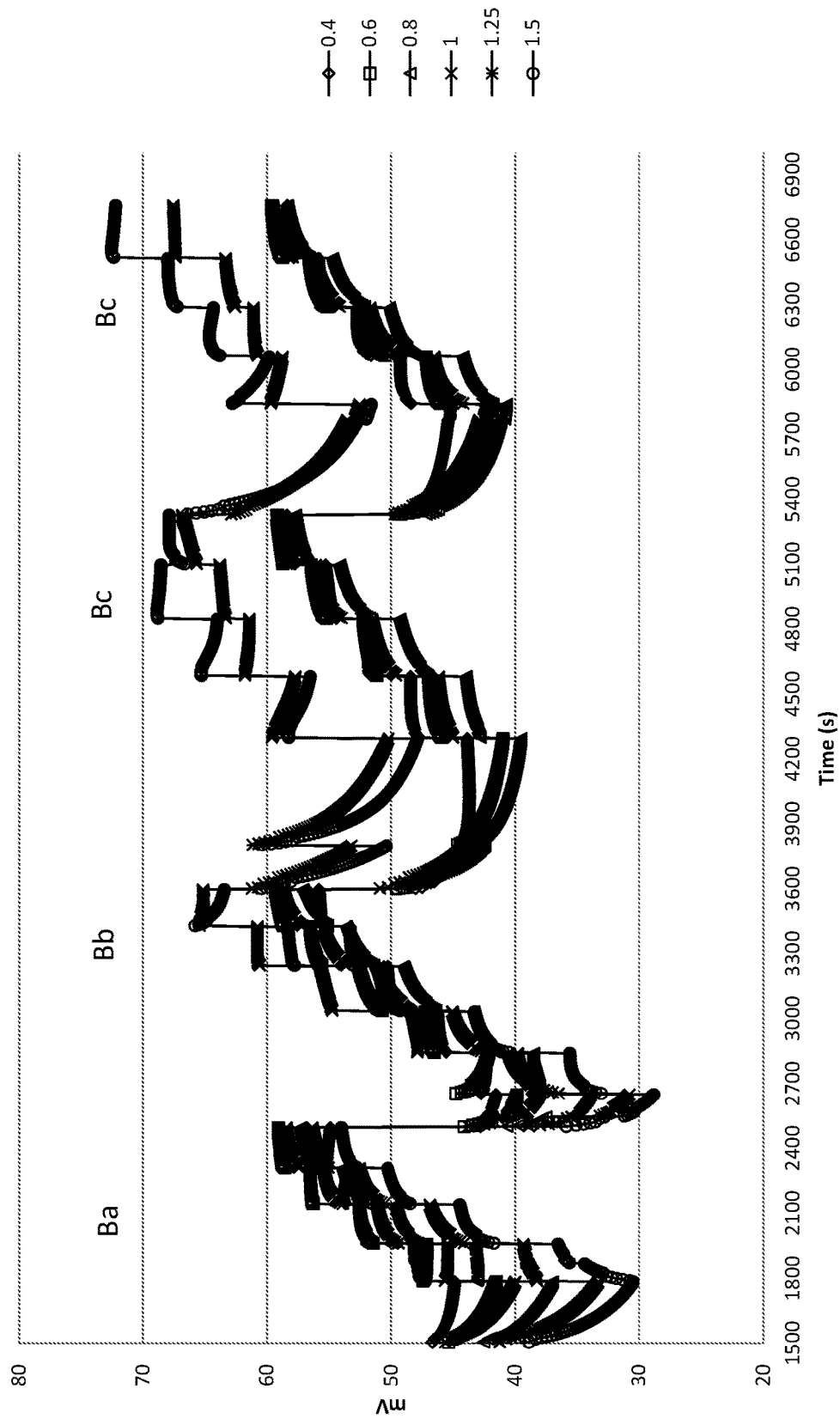
Figure 2:
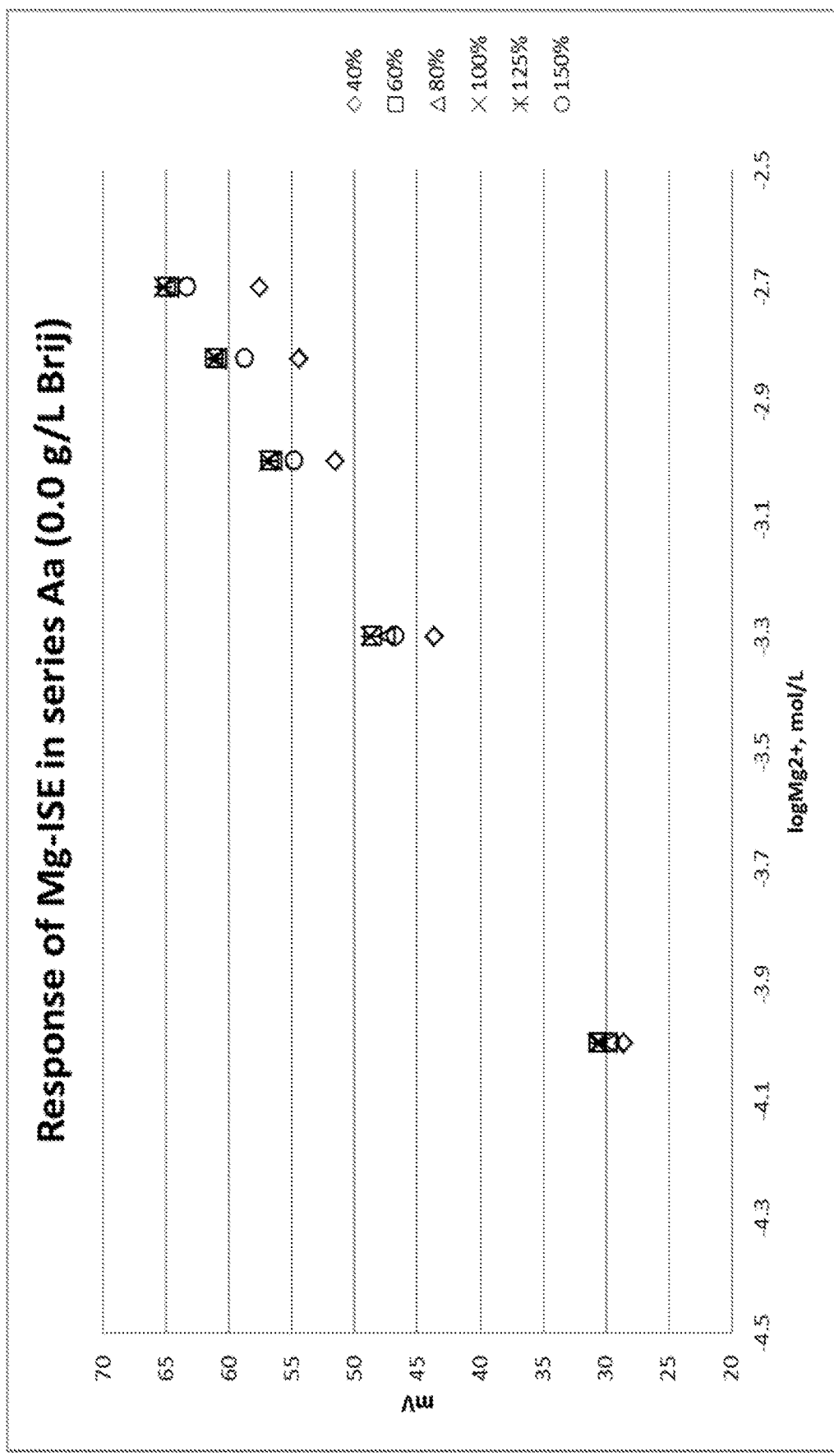
FIG. 2 graphically illustrates response slope plots for the six Mg-ISEs from FIG. 1A upon exposure to Series Aa (0.0 g/L Brij surfactant in a simple $MgCl_2$ solution).
Figure 3:
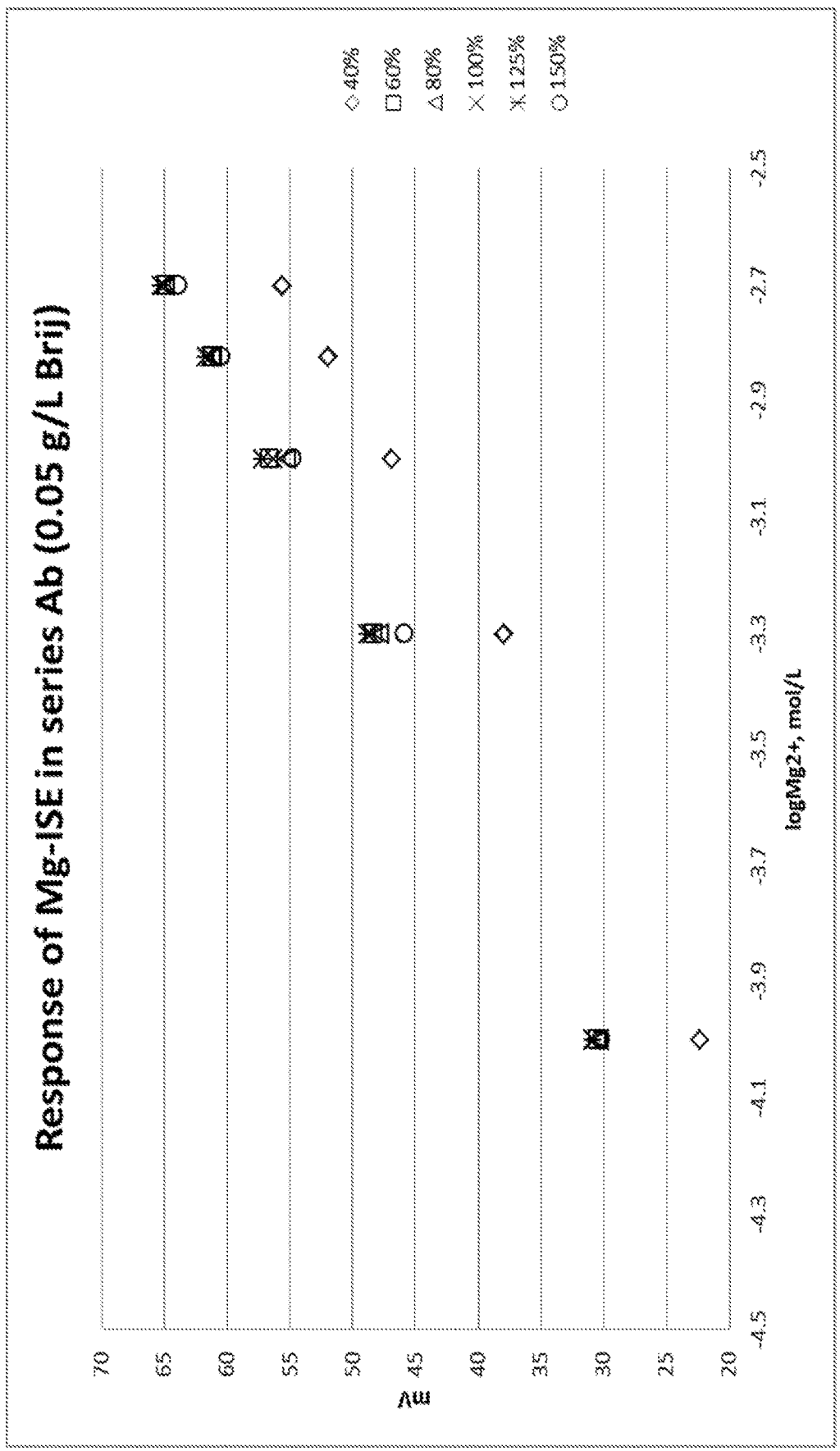
FIG. 3 graphically illustrates response slope plots for the six Mg-ISEs from FIG. 1A upon exposure to Series Ab (0.05 g/L Brij surfactant in a simple $MgCl_2$ solution).
Figure 4:
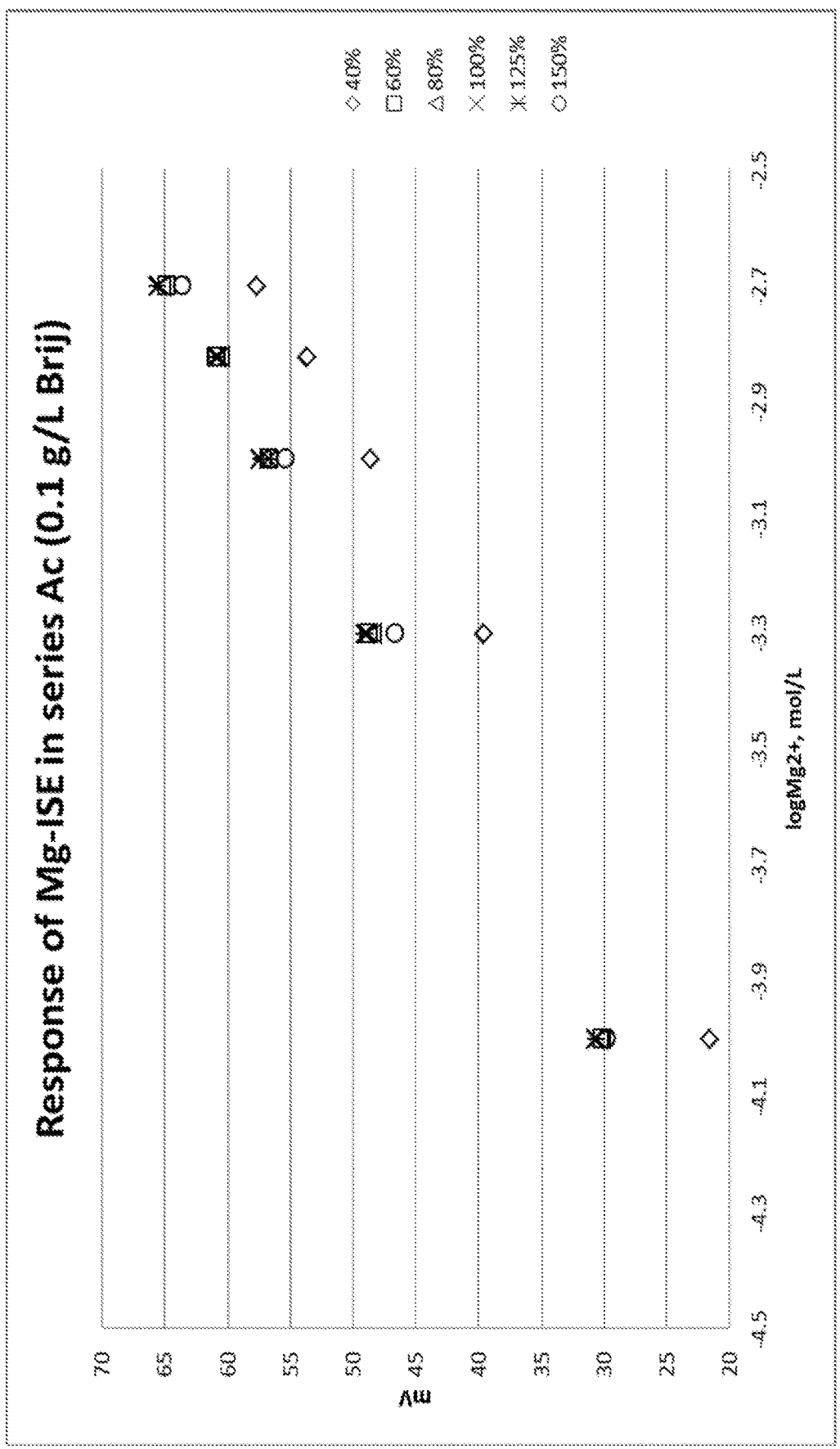
FIG. 4 graphically illustrates response slope plots for the six Mg-ISEs from FIG. 1A upon exposure to Series Ac (0.1 g/L Brij surfactant in a simple $MgCl_2$ solution).
Figure 5:
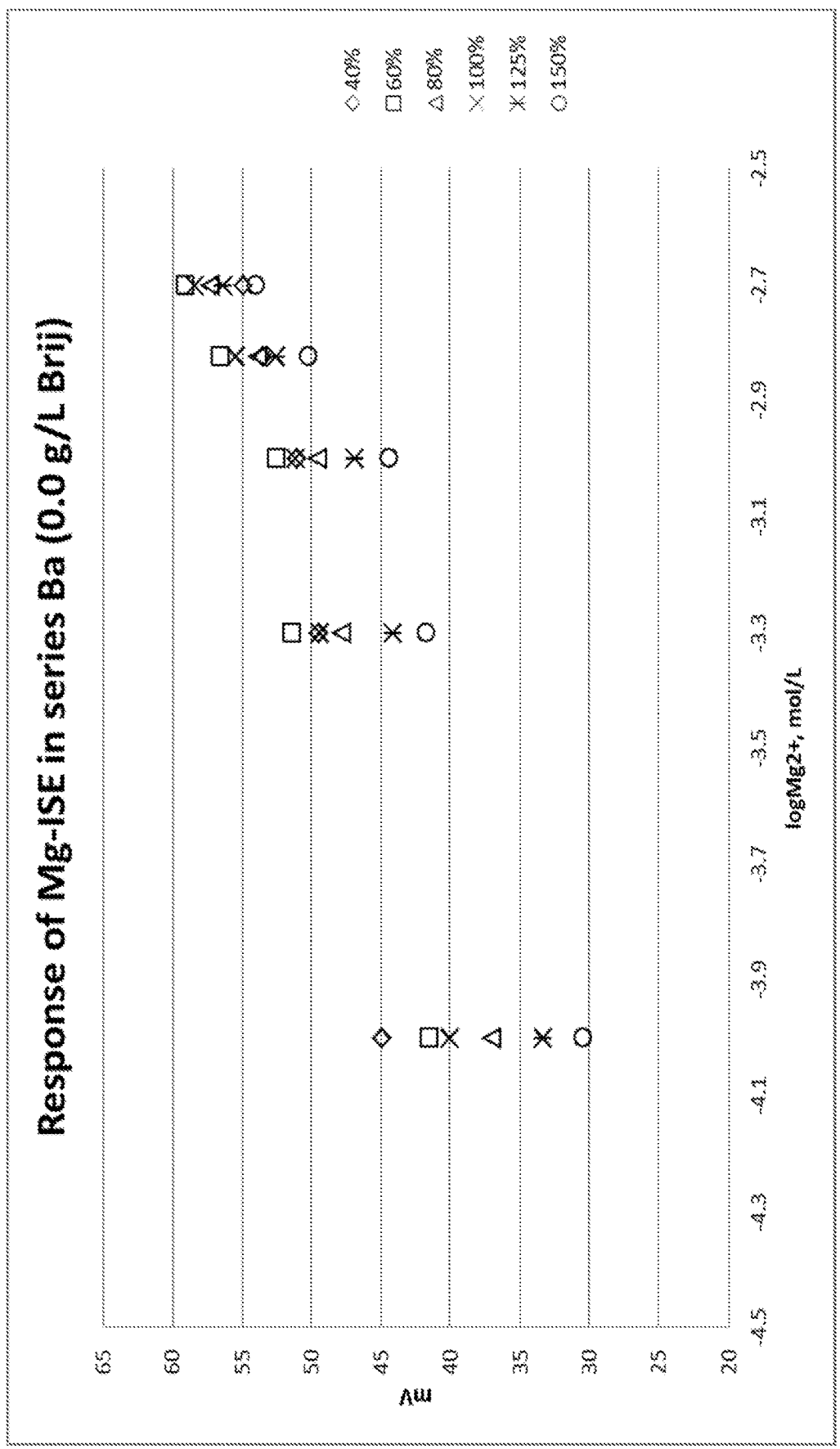
FIG. 5 graphically illustrates response slope plots for the six Mg-ISEs from FIG. 1B upon exposure to Series Ba (0.0 g/L Brij surfactant in an electrolyte background solution).
Figure 6:
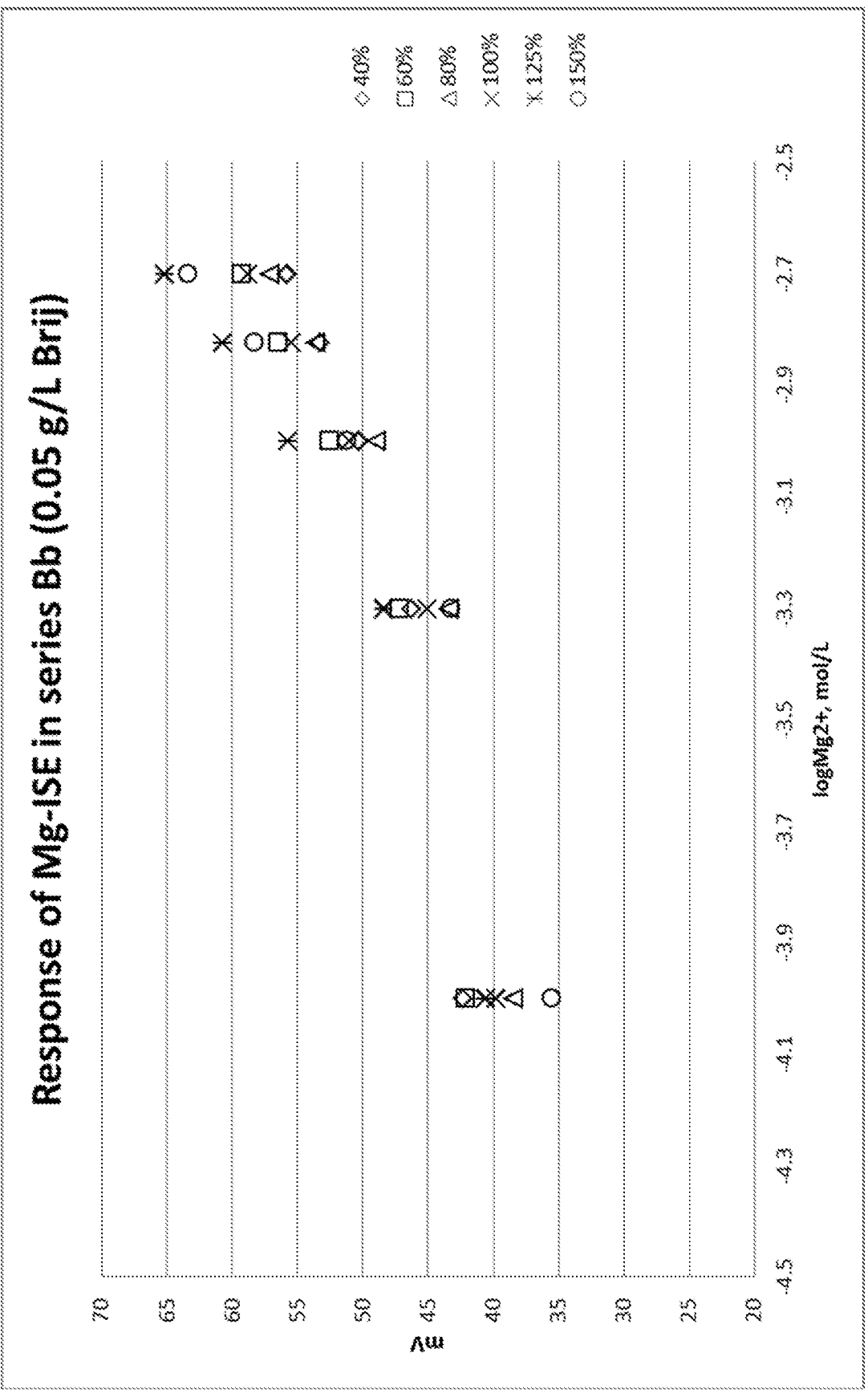
FIG. 6 graphically illustrates response slope plots for the six Mg-ISEs from FIG. 1B upon exposure to Series Bb (0.05 g/L Brij surfactant in an electrolyte background solution).
Figure 7:
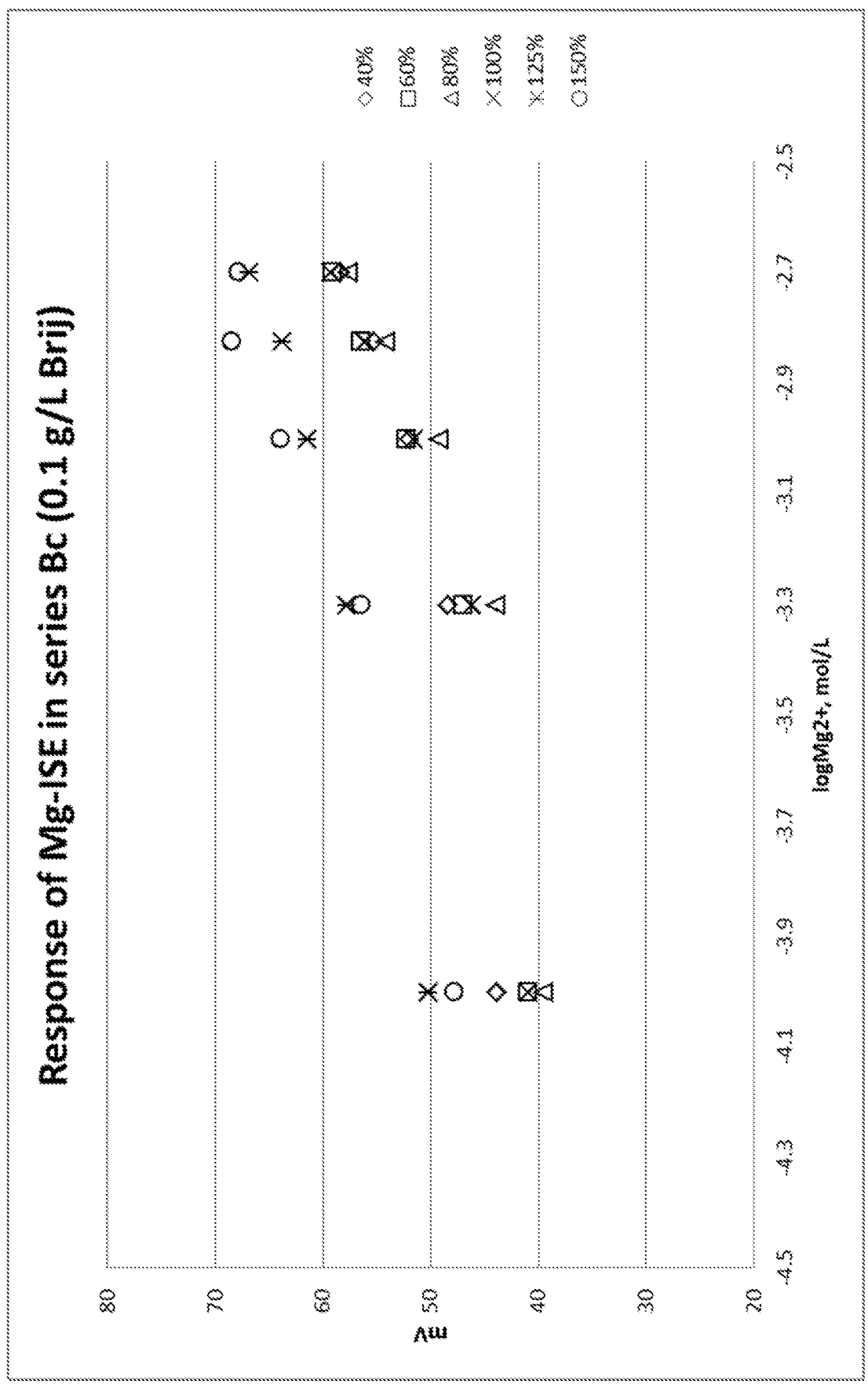
FIG. 7 graphically illustrates response slope plots for the six Mg-ISEs from FIG. 1B upon exposure to Series Bc (0.1 g/L Brij surfactant in an electrolyte background solution).
Figure 8:
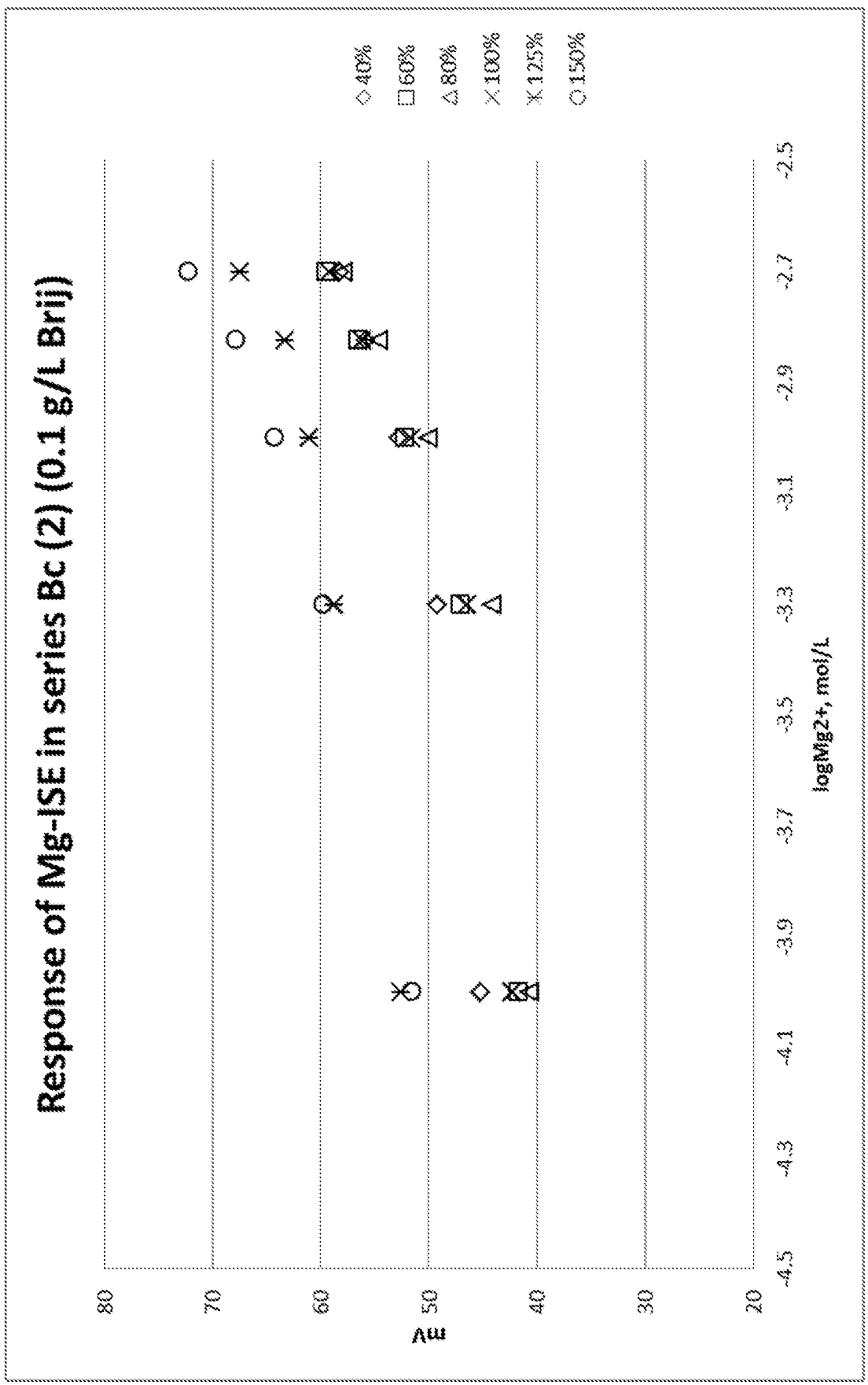
FIG. 8 graphically illustrates response slope plots for the six Mg-ISEs from FIG. 1B upon exposure to Series Bc(2) (0.1 g/L Brij surfactant in an electrolyte background solution).

FIGS. 1A and 1B show the raw response of the six electrodes with different borate:ionophore ratios in solution matrix. In the simple $MgCl_2$ solution series Aa, Ab, and Ac (FIG. 1A), no significant mV drifts were observed across the six different electrode formulations. In addition, a significant difference regarding mV drift, slope, and kinetics was not observed for the six different electrode formulations. The response slope of series Aa, Ab, and Ac are shown in Table 2.

TABLE 1

Matrix for Testing Impact on Mg-ISE From Brij700 and/or Electrolyte Background

| Simple $Mg^{2+}$ solutions | A1 | A2 | A3 | A4 | A5 |
|---|---|---|---|---|---|
| tMg (mM) | 0.1 | 0.5 | 1.0 | 1.5 | 2.0 |
| a (g/L Brij) | 0 | 0 | 0 | 0 | 0 |
| b (g/L Brij) | 0.05 | 0.05 | 0.05 | 0.05 | 0.05 |
| c (g/L Brij) | 0.10 | 0.10 | 0.10 | 0.10 | 0.10 |
| $Mg^{2+}$ solutions with fixed Na+ and $Ca^{2+}$ | B1 | B2 | B3 | B4 | B5 |
| tMg (mM) | 0.1 | 0.5 | 1.0 | 1.5 | 2.0 |
| tCa (mM) | 1.0 | 1.0 | 1.0 | 1.0 | 1.0 |
| NaCl (mM) | 150 | 150 | 150 | 150 | 150 |
| pH | 7.4 | 7.4 | 7.4 | 7.4 | 7.4 |
| MOPS (mM) | 20 | 20 | 20 | 20 | 20 |
| a (g/L Brij) | 0 | 0 | 0 | 0 | 0 |
| b (g/L Brij) | 0.05 | 0.05 | 0.05 | 0.05 | 0.05 |
| c (g/L Brij) | 0.10 | 0.10 | 0.10 | 0.10 | 0.10 |

In the electrolyte background solution series Ba, Bb, and Bc (FIG. 1B), a large difference was observed among the six different sensor formulations. Sensors with 125 mol % and 150 mol % borate:ionophore ratios showed a high level of mV drift in low $Mg^{2+}$ solutions and high Brij700 level solutions. Sensors with borate:ionophore ratios of 125 mol % and 150 mol % showed slower reversibility or carryover effect when the testing solution was alternated from high to low. Sensors with a borate:ionophore ratio of 40 mol % had a degraded response slope when compared to the slope observed with the sensors having a >60 mol % borate:ionophore ratio. Among the sensor formulations with borate:ionophore ratios from 60 mol % to 100 mol %, the sensor with 80 mol % exhibited the best response slope in solution series of varying surfactant levels (shown in Table 2). At a surfactant (Brij700) concentration of 0.05 g/L (i.e., the concentration present in current reagents), the sensor having a borate:ionophore ratio of 80 mol % yielded a slope of 13.81 mV/d (without selectivity coefficient correction).

TABLE 2

Slopes of Mg-ISE in Solution Matrix for Studying Brij700 Impact to Mg-ISE

| Borate % | 40% | 60% | 80% | 100% | 125% | 150% |
|---|---|---|---|---|---|---|
| Aa | 22.35 | 26.42 | 26.78 | 26.29 | 26.42 | 25.51 |
| Ab | 25.51 | 26.42 | 26.32 | 26.23 | 26.46 | 25.98 |
| Ac | 26.99 | 25.17 | 25.21 | 25.07 | 25.13 | 24.37 |
| Ba | 7.45 | 12.79 | 14.69 | 13.38 | 16.78 | 17.17 |
| Bb | 10.06 | 12.97 | 13.81 | 14.22 | 18.40 | 20.67 |
| Bc | 10.56 | 13.74 | 13.43 | 13.68 | 12.26 | 16.59 |
| Bc (2) | 9.70 | 13.26 | 12.92 | 12.61 | 10.39 | 15.06 |

*These slopes are not corrected with selectivity coefficient, and concentrations are not corrected to activities.

FIGS. 2-8 exhibit the response slope plots of the six sensors in the different solution series. In the simple solution series of Aa, Ab, and Ac, no obvious difference was observed with addition of surfactant; the sensor with 40 mol % showed some mV and slope variation in low [$Mg^{2+}$] solutions (A5a, A5b, A5c). This result implies that surfactant induced CM-4 is not likely associated to Brij700-$Mg^{2+}$ interaction either in solution or at the membrane interface.

In the electrolyte background solution series of Ba, Bb, and Bc, obvious differences were seen among the six sensors with varying borate:ionophore ratios. The detection limits of all of the sensors were elevated due to the interferences seen with $Ca^{2+}$ (1.0 mM) and Na+ (150 mM). At the low [$Mg^{2+}$] end of the solutions (B5a, B5b and B5c), kinetics were associated to the borate:ionophore ratio, where membranes with high borate:ionophore ratios (and thus high concentrations of borate) tended to have slower responses. As the Brij700 levels in the solution series increased, the membranes with high borate:ionophore ratios (125 mol % and 150 mol %) exhibited positive mV drift, and the reversibility from high [$Mg^{2+}$] to low [$Mg^{2+}$] was degraded. Membranes with borate:ionophore ratios from 60 mol % to 100 mol % did not show significant variation of signals and response slopes with increasing Brij700 levels from 0.00 to 0.05 to 0.1 g/L. The sensor with the 40 mol % borate:ionophore ratio exhibited a stable response mV but had a degraded slope (sensitivity). Combining the observations from solution series A, the CM-4 interference to the membranes with high borate:ionophore ratios is likely driven by the surfactant-$Ca^{2+}$ and $Na^+$ at the sensor membrane interface. Previous investigations with impedance spectroscopy and theoretical calculation indicated a thin surfactant layer on PVC/borate membrane interface that works as an ion exchanger. With this model, monovalent cations would be favored over divalent cations, and $Ca^{2+}$ would be favored over $Mg^{2+}$. At the prior art "optimal borate:ionophore ratio of 150 mol %", surfactant may even penetrate into the membrane and act as a stronger ion-exchanger that competes with the Mg$^{2+}$-ETH5506 interaction. This could eventually change the Mg-ISE's response reversibility.

Among these sensor formulations, the borate:ionophore ratio at 80 mol % was chosen based upon its stability in surfactant and its sensitivity to Mg$^{2+}$.

Figure 9:
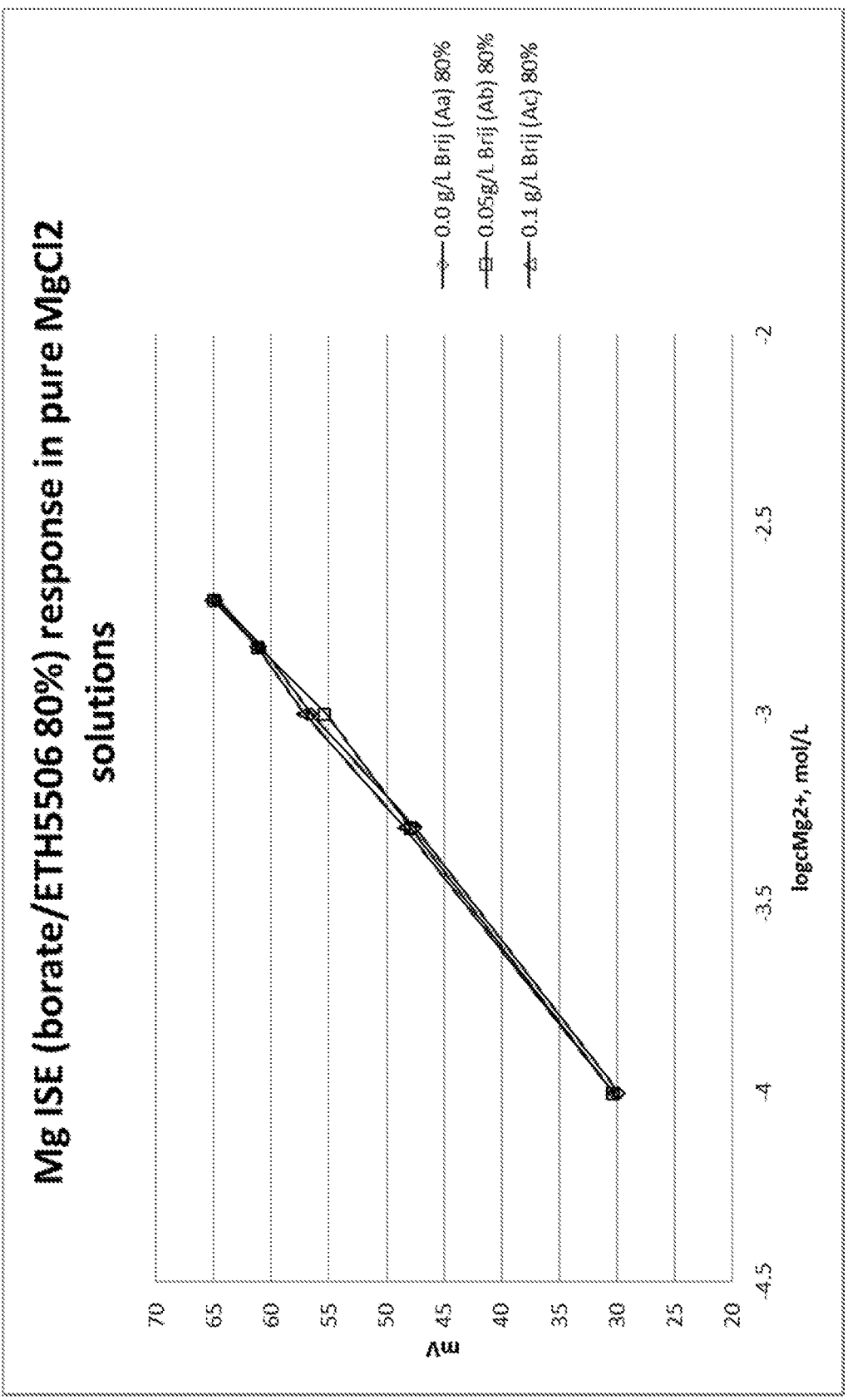
FIG. 9 graphically illustrates response slope plots for the Mg-ISE with a borate:ETH5506 ratio of 80 mol % upon exposure to Series Aa, Ab, and Ac (0.0, 0.05, and 0.1 g/L Brij surfactant, respectively, in simple $MgCl_2$ solutions).
Figure 10:
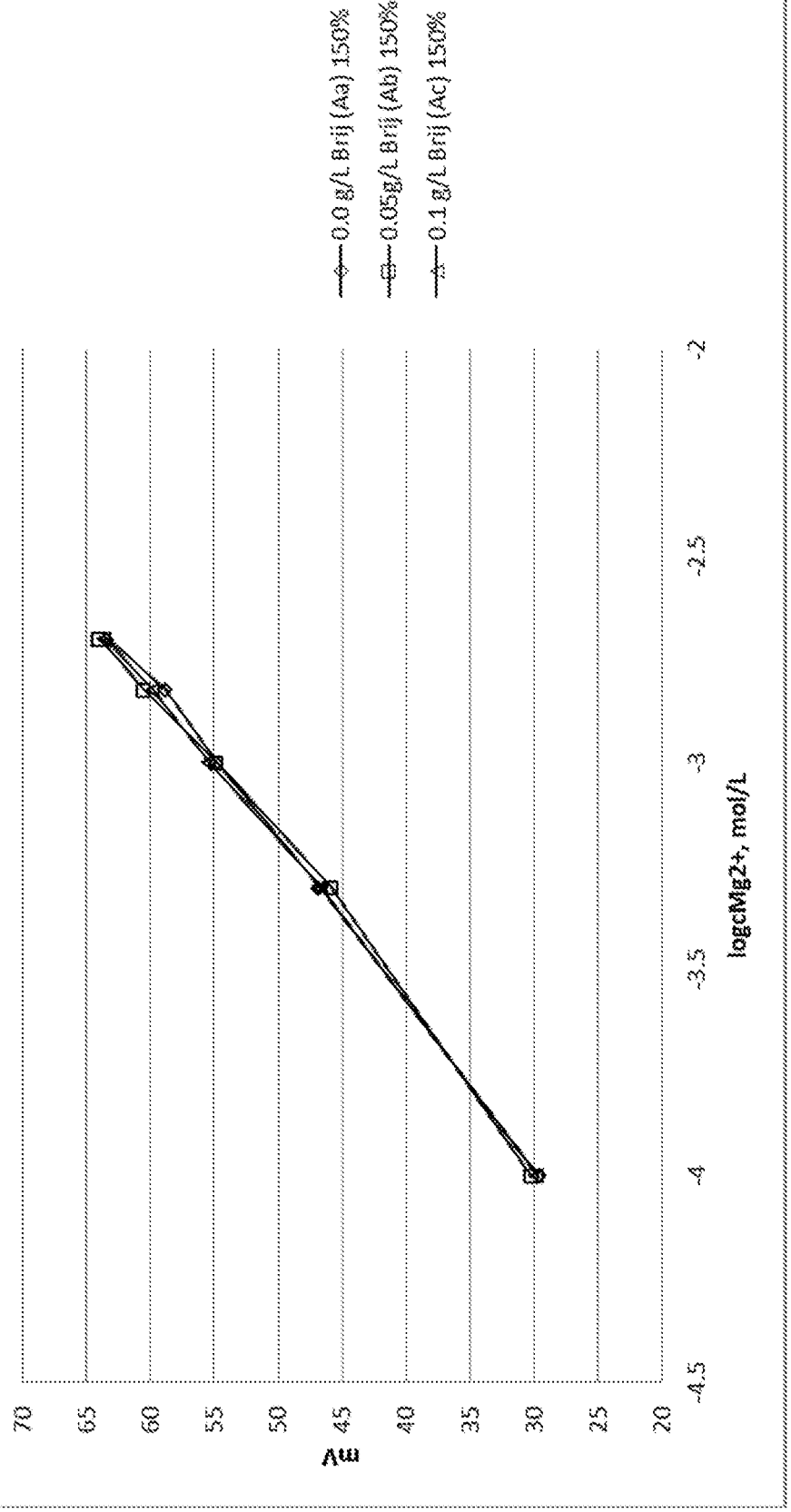
FIG. 10 graphically illustrates response slope plots for the Mg-ISE with a borate:ETH5506 ratio of 150 mol % upon exposure to Series Aa, Ab, and Ac (0.0, 0.05, and 0.1 g/L Brij surfactant, respectively, in simple $MgCl_2$ solutions).

In the pure MgCl$_2$ solution series, there is no difference between the membrane containing a 80 mol % borate:ionophore ratio formulation and the membrane containing a 150 mol % borate:ionophore ratio formulation; as shown in FIGS. 9 and 10, both showed identical response slopes (25-26 mV/Dec without activity correction).

Figure 11:
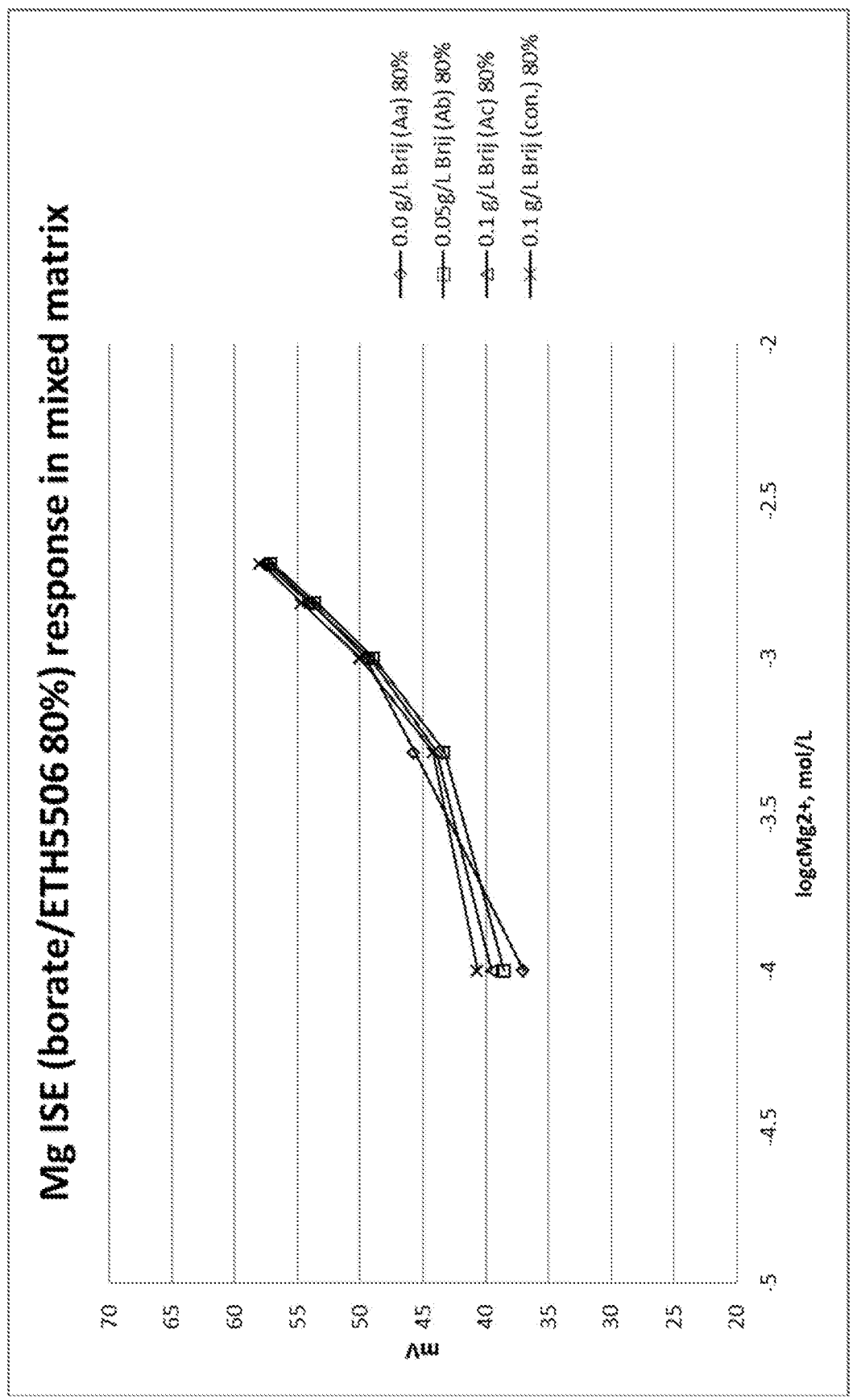
FIG. 11 graphically illustrates response slope plots for the Mg-ISE with a borate:ETH5506 ratio of 80 mol % upon exposure to Series Ba, Bb, Bc, and Bc(2) (0.0, 0.05, 0.1, and 0.1 g/L Brij surfactant, respectively, in electrolyte background solutions).
Figure 12:
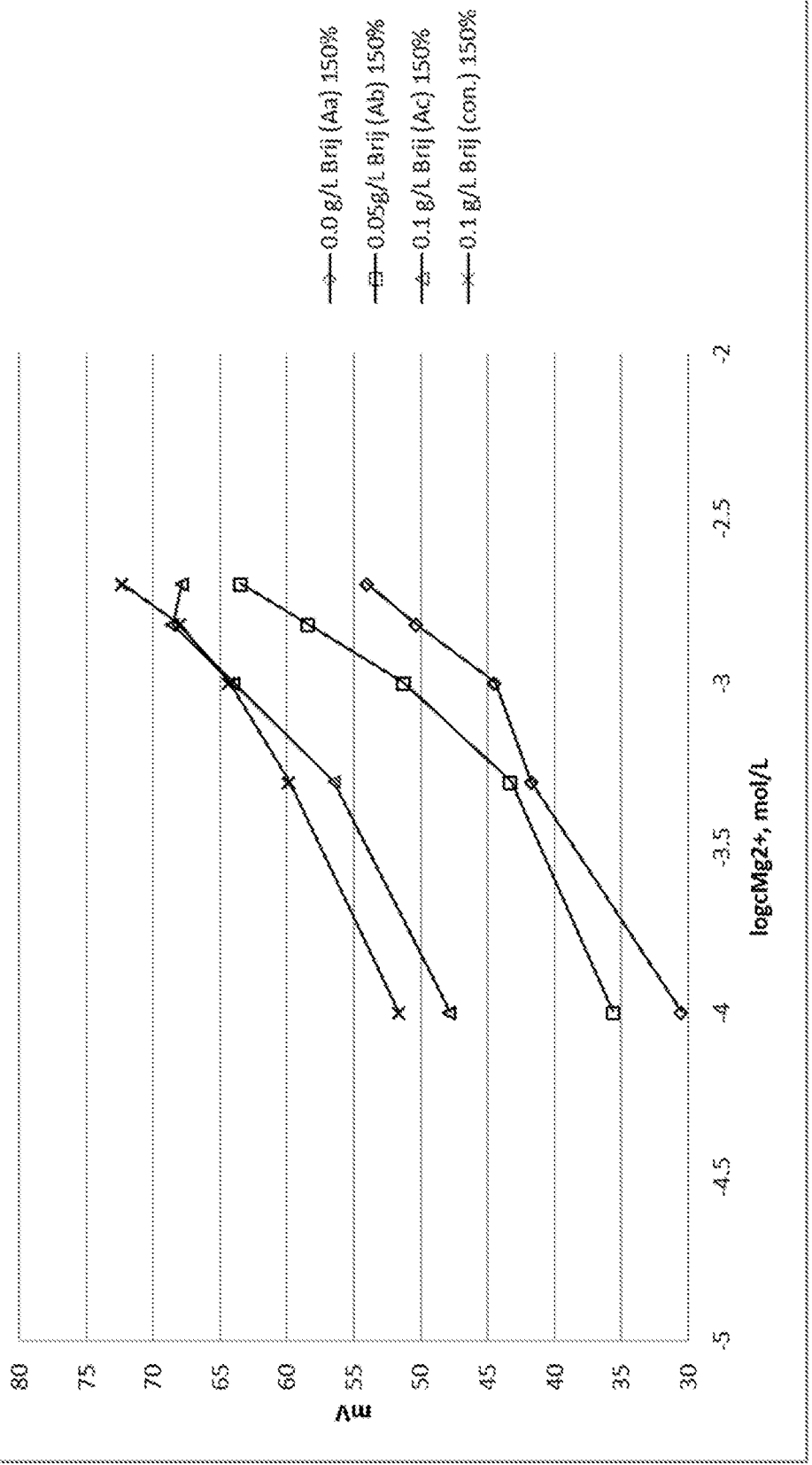
FIG. 12 graphically illustrates response slope plots for the Mg-ISE with a borate:ETH5506 ratio of 150 mol % upon exposure to Series Ba, Bb, Bc, and Bc(2) (0.0, 0.05, 0.1, and 0.1 g/L Brij surfactant, respectively, in electrolyte background solutions).

In the background solution series with no surfactant (Ba series), the sensor having a borate:ionophore ratio of 150 mol % exhibited a higher response slope than the sensor having a borate:ionophore ratio of 80 mol % (17.2 mV/Dec vs. 14.7 mV/Dec). Such a difference was contributed by the selectivity difference against Ca$^{2+}$ (0.01 vs. 0.5) as well as Na$^+$ (very low). In the background solution series with Brij700 (Bb series and Bc series), the Brij700 surfactant caused a huge impact on the sensor having a borate:ionophore ratio of 150 mol % with respect to its mV stability (especially at the low end of ~0.5 mM), reversibility, and response kinetics (FIG. 12). However, as seen in FIG. 11, no significant impact was observed for the sensor having a borate:ionophore ratio of 80 mol %.

Figure 13:
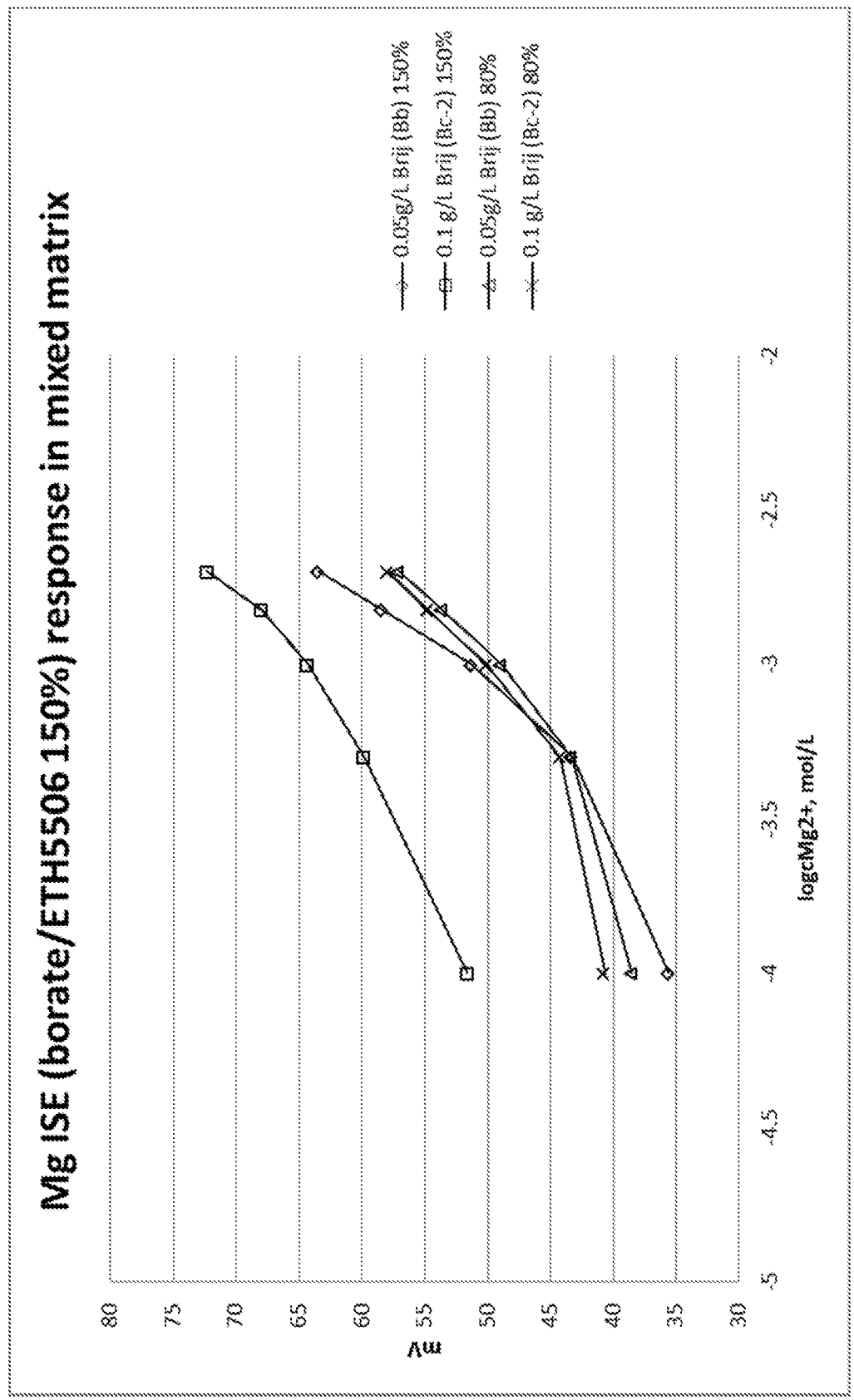
FIG. 13 graphically illustrates the signal mV shifts between the two solution series Bc and Bc(2) (i.e., 0.1 g/L Brij surfactant in electrolyte background solutions) for the Mg-ISE's with borate:ETH5506 ratios of 80 mol % and 150 mol %.
Figure 14:
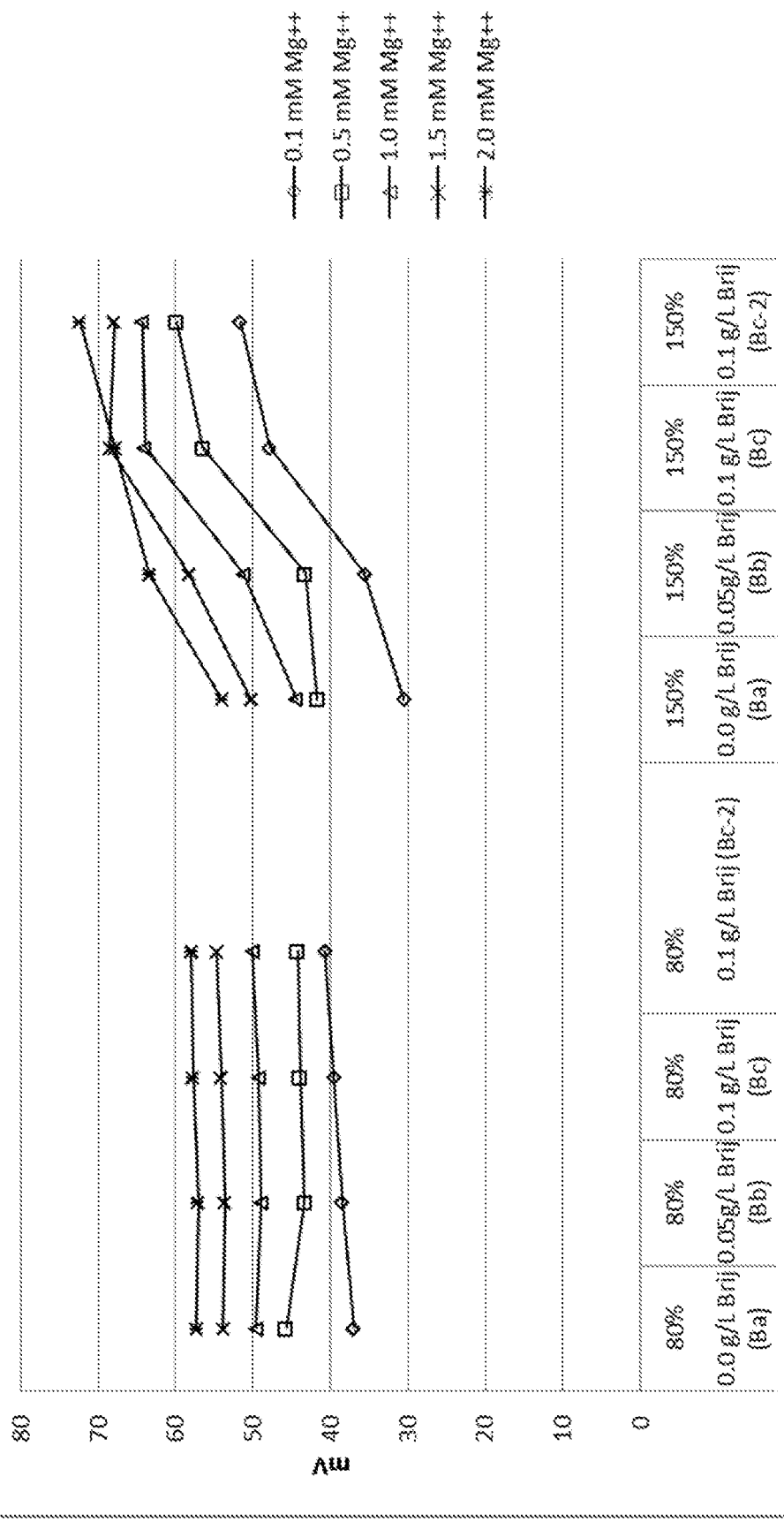
FIG. 14 graphically illustrates a response signal mV shift (by Brij700 surfactant) comparison between the two Mg-ISE's with borate:ETH5506 ratios of 80 mol % and 150 mol % upon exposure to Series Ba, Bb, Bc, and Bc(2) (0.0, 0.05, 0.1, and 0.1 g/L Brij surfactant, respectively, in electrolyte background solutions) and upon exposure to 0.1, 0.5 1.0, 1.5, or 2.0 mM magnesium ion.

As shown in FIGS. 13-14, comparison of the sensor having a borate:ionophore ratio of 150 mol % to the sensor having a borate:ionophore ratio of 80 mol % indicated that the 150 mol % borate:ionophore sensor had better response performance in the solution series with no Brij700 surfactant. However, such performance was degraded when the Brij 700 surfactant was present. On the contrary, the sensor having a borate:ionophore ratio of 80 mol % had less sensitivity and selectivity than that observed for the 150 mol % sensor. However, the positive point of such sensor is its stable response in the presence of Brij700 in solution. This stability assists the Mg-ISE calibration process by providing stable results. The compensated slope and selectivity can be corrected with an algorithm (based on selectivity and offset).

Thus, membrane formulations with borate:ionophore ratios in a range of about 60 mol % to about 100 mol % fall within the scope of the presently disclosed and claimed inventive concept(s), based on the above results and analyses, with the membrane formulation of about 80 mol % borate:ionophore (ETH5506) ratio exhibiting an optimal (but non-limiting) membrane formulation.

Therefore, in accordance with the presently disclosed and claimed inventive concept(s), there has been provided magnesium sensing membrane, as well as kits containing same and methods of production and use thereof, that fully satisfy the objectives and advantages set forth hereinabove. Although the presently disclosed and claimed inventive concept(s) has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed and claimed inventive concept(s).

The following is a list of non-limiting illustrative embodiments of the inventive concepts disclosed herein:

1. A magnesium sensing membrane for an illustrative potentiometric ion selective electrode that detects ionized magnesium in a biological sample, the membrane comprising:

an ionophore having a tripodal stereochemical structure;

a lipophilic borate salt, wherein the lipophilic borate salt is present in an amount that provides a mol ratio of lipophilic borate salt to ionophore in a range of from about 60 mol % to about 100 mol %; and a polymer matrix in which the ionophore and lipophilic borate salt are disposed, wherein the polymer matrix comprises a polymer and a plasticizer.

2. The illustrative magnesium sensing membrane of embodiment 1, wherein the ionophore has at least one malonic imide functional group.

3. The illustrative magnesium sensing membrane of embodiment 1, wherein the ionophore is represented by the structure of Formula I:

Formula I

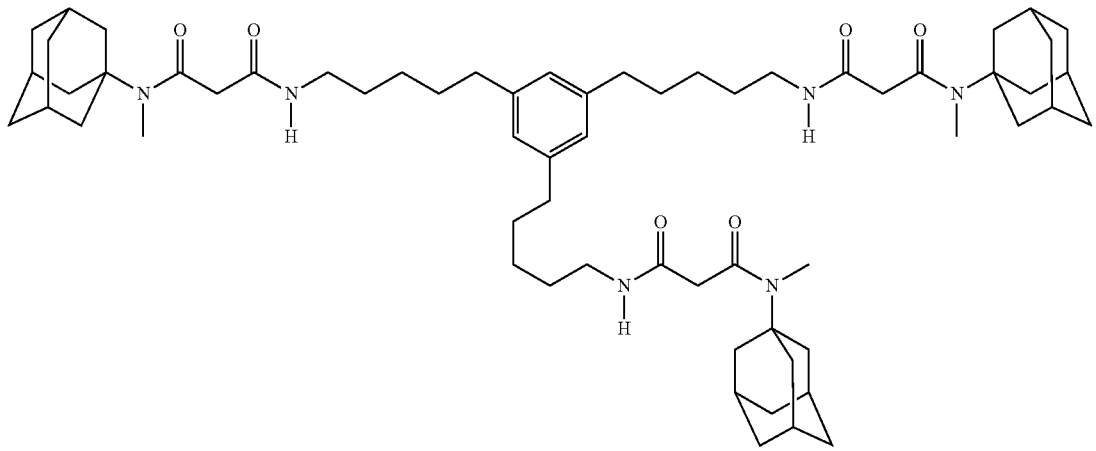

4. The illustrative magnesium sensing membrane of embodiment 1, wherein the ionophore is represented by the structure of Formula II:

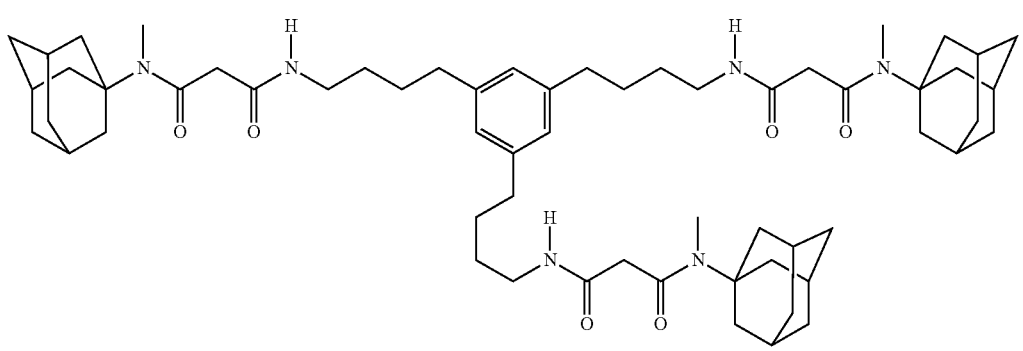

Formula II

5. The illustrative magnesium sensing membrane of embodiment 1, wherein the ionophore is represented by the structure of Formula III:

group consisting of 2-nitrophenyl octyl ether, 2-Nitrophenyl dodecyl ether and [12-(4-ethylphenyl)dodecyl] 2-nitrophenyl ether.

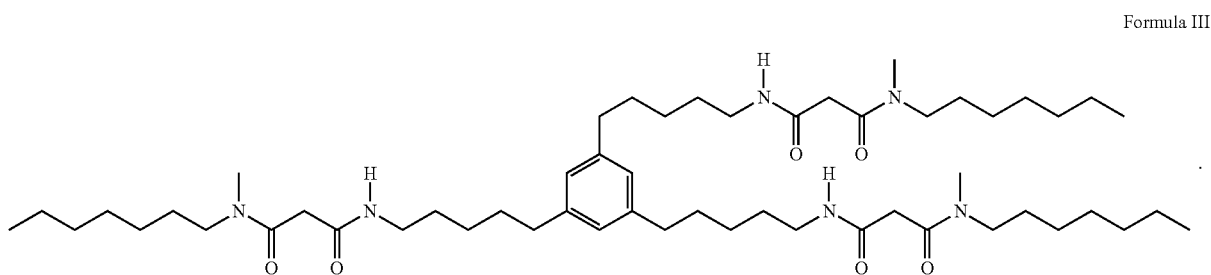 [SMILES: CCCCCCCN(C)C(=O)CC(=O)NCCCCCc1cc(CCCCCNC(=O)CC(=O)N(C)CCCCCCC)cc(CCCCCNC(=O)CC(=O)N(C)CCCCCCC)c1]

Formula III

6. The illustrative magnesium sensing membrane of embodiment 1, wherein the ionophore is represented by the structure of Formula IV:

9. The illustrative magnesium sensing membrane of embodiment 1, wherein the mol ratio of lipophilic borate salt to ionophore is about 80 mol %.

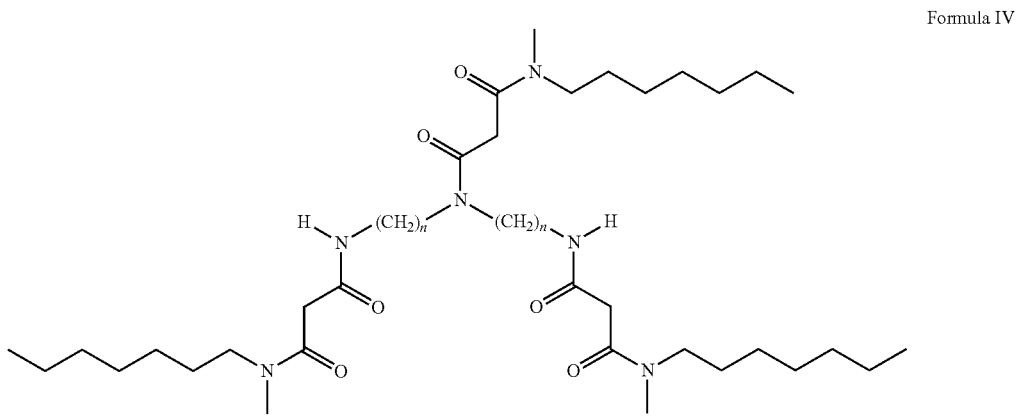

Formula IV wherein n is in the range of from about 6 to about 8.

7. The illustrative magnesium sensing membrane of embodiment 1, wherein the lipophilic borate salt is selected from the group consisting of potassium tetrakis[3,5-bis(trifluoromethyl)phenyl]borate; sodium tetrakis[3,5-bis(trifluoromethyl)phenyl]borate; and potassium tetrakis(4-chlorophenyl)borate.

8. The illustrative magnesium sensing membrane of embodiment 1, wherein the plasticizer is selected from the 10. The illustrative magnesium sensing membrane of embodiment 1, wherein the polymer is selected from the group consisting of poly(vinyl chloride), polyurethane, and combinations thereof.

11. The illustrative magnesium sensing membrane of embodiment 1, further defined as a solid-state, planar magnesium sensing membrane.

12. An illustrative potentiometric ion selective electrode that detects ionized magnesium in a biological sample, the potentiometric ion selective electrode comprising the magnesium sensing membrane of any of embodiments 1-11.

13. An illustrative method, comprising the steps of:
contacting the potentiometric ion selective electrode of embodiment 12 with a biological sample; and
measuring a level of magnesium ion in the biological sample using the potentiometric ion selective electrode.

14. The illustrative method of embodiment 13, further comprising the step of contacting the potentiometric ion selective electrode with a reagent comprising a poly(ethylene oxide) surfactant.

15. The illustrative method of embodiment 14, wherein the poly(ethylene oxide) surfactant is represented by the structure of Formula

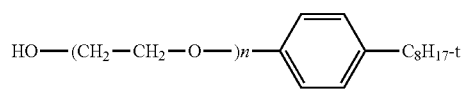

Formula V wherein n is in the range of from about 9 to about 10.

16. The illustrative method of embodiment 14, wherein the poly(ethylene oxide) surfactant is represented by the structure of Formula

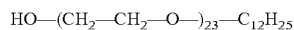

Formula VI

17. The illustrative method of embodiment 14, wherein the poly(ethylene oxide) surfactant is represented by the structure of Formula VII:

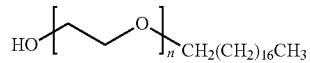

Formula VII wherein n is about 100.

18. The illustrative method of embodiment 14, wherein the concentration of the poly(ethylene oxide) surfactant is less than about 100 mg/L.

19. An illustrative kit comprising:
the potentiometric ion selective electrode of embodiment 12; and
at least one reagent comprising a poly(ethylene oxide) surfactant.

20. The illustrative kit of embodiment 19, wherein the at least one reagent is one or more calibration reagents.

21. The illustrative kit of embodiment 20, further comprising at least one additional reagent comprising a poly(ethylene oxide) surfactant, wherein the at least one additional reagent is a wash reagent, a quality control reagent, and another calibration reagent.

22. The illustrative kit of any of embodiments 19-21, wherein the at least one reagent is one or more quality control reagents.

23. The illustrative kit of embodiment 22, further comprising at least one additional reagent comprising a poly(ethylene oxide) surfactant, wherein the at least one additional reagent is a wash reagent, a calibration reagent, and another quality control reagent.

24. The illustrative kit of embodiment 19, wherein the reagent is one or more wash reagents.

25. The illustrative kit of embodiment 24, further comprising at least one additional reagent comprising a poly(ethylene oxide) surfactant, wherein the at least one additional reagent is a calibration reagent, a quality control reagent, and another wash reagent.

26. The illustrative kit of embodiment 19, further comprising instructions for rinsing, calibrating, and operating the magnesium ion sensor.

27. The illustrative kit of embodiment 19, wherein the concentration of the poly(ethylene oxide) surfactant in the at least one reagent is less than about 100 mg/L.

28. The illustrative kit embodiment 19, wherein the poly(ethylene oxide) surfactant of the at least one reagent is represented by the structure of Formula V:

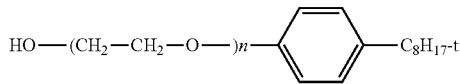

Formula V wherein n is in the range of from about 9 to about 10.

29. The kit of embodiment 19, wherein the poly(ethylene oxide) surfactant of the at least one reagent is represented by the structure of Formula VI:

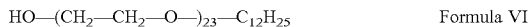

Formula VI

30. The kit of embodiment 19, wherein the poly(ethylene oxide) surfactant of the at least one reagent is represented by the structure of Formula VII:

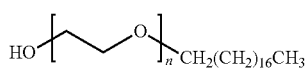

Formula VII wherein n is about 100.

What is claimed is:

1. A potentiometric ion selective electrode that detects ionized magnesium in a biological sample, the potentiometric ion selective electrode comprising:
a magnesium sensing membrane that detects ionized magnesium in a biological sample, the membrane comprising:
an ionophore having a tripodal stereochemical structure;
a lipophilic borate salt, wherein the lipophilic borate salt is present in an amount that provides a mol ratio of lipophilic borate salt to ionophore in a range of from about 75 mol % to about 100 mol %; and
a polymer matrix in which the ionophore and lipophilic borate salt are disposed, wherein the polymer matrix comprises a polymer and a plasticizer, wherein the polymer is selected from the group consisting of poly(vinyl chloride), polyurethane, and combinations thereof;
wherein the potentiometric ion selective electrode is more selective to $Mg^{2+}$ than to $Ca^{2+}$; and
wherein the potentiometric ion selective electrode is substantially stable upon exposure to a reagent comprising a poly(ethylene oxide) surfactant.

2. The potentiometric ion selective electrode of claim 1, wherein the lipophilic borate salt is selected from the group consisting of potassium tetrakis[3,5-bis(trifluoromethyl)phenyl]borate; sodium tetrakis[3,5-bis(trifluoromethyl)phenyl]borate; and potassium tetrakis(4-chlorophenyl)borate.

3. The potentiometric ion selective electrode of claim 1, wherein the plasticizer is selected from the group consisting of 2-nitrophenyl octyl ether, 2-Nitrophenyl dodecyl ether and [12-(4-ethylphenyl)dodecyl] 2-nitrophenyl ether.

4. The potentiometric ion selective electrode of claim 1, wherein the mol ratio of lipophilic borate salt to ionophore is in a range of from about 75 mol % to about 85 mol %.

5. The potentiometric ion selective electrode of claim 1, wherein the mol ratio of lipophilic borate salt to ionophore is about 80 mol %.

6. The potentiometric ion selective electrode of claim 1, wherein the mol ratio of lipophilic borate salt to ionophore is in a range of from about 75 mol % to about 85 mol %, and wherein the lipophilic borate salt is selected from the group consisting of potassium tetrakis[3,5-bis(trifluoromethyl) phenyl]borate; sodium tetrakis[3,5-bis(trifluoromethyl) phenyl]borate; and potassium tetrakis(4-chlorophenyl)borate.

7. A method, comprising the steps of:
contacting a potentiometric ion selective electrode with a biological sample, wherein the potentiometric ion selective electrode comprises a magnesium sensing membrane that detects ionized magnesium in a biological sample, and wherein the membrane comprises: (i) an ionophore having a tripodal stereochemical structure; (ii) a lipophilic borate salt present in an amount that provides a mol ratio of lipophilic borate salt to ionophore in a range of from about 75 mol % to about 100 mol %; and (iii) a polymer matrix in which the ionophore and lipophilic borate salt are disposed, wherein the polymer matrix comprises a polymer and a plasticizer, wherein the polymer is selected from the group consisting of poly(vinyl chloride), polyurethane, and combinations thereof; and wherein the potentiometric ion selective electrode is more selective to $Mg^{2+}$ than to $Ca^{2+}$, and wherein the potentiometric ion selective electrode is substantially stable upon exposure to a reagent comprising a poly(ethylene oxide) surfactant; and
measuring a level of magnesium ion in the biological sample using the potentiometric ion selective electrode.

8. The method of claim 7, further comprising the step of contacting the potentiometric ion selective electrode with a reagent comprising a poly(ethylene oxide) surfactant.

9. The method of claim 8, wherein the poly(ethylene oxide) surfactant is represented by the structure of Formula V, VI, or VII:

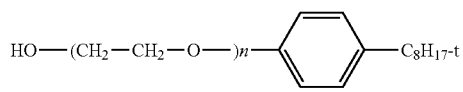

Formula V

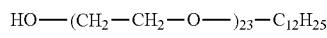

Formula VI

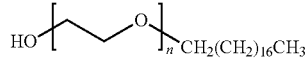

Formula VII wherein n in Formula V is in the range of from 9 to 10, and n in Formula VII is 100.

10. The method of claim 8, wherein the concentration of the poly(ethylene oxide) surfactant is less than 100 mg/L.

11. A kit comprising:
a potentiometric ion selective electrode comprising a magnesium sensing membrane that detects ionized magnesium in a biological sample, wherein the membrane comprises: (i) an ionophore having a tripodal stereochemical structure; (ii) a lipophilic borate salt present in an amount that provides a mol ratio of lipophilic borate salt to ionophore in a range of from about 75 mol % to about 100 mol %; and (iii) a polymer matrix in which the ionophore and lipophilic borate salt are disposed, wherein the polymer matrix comprises a polymer and a plasticizer, wherein the polymer is selected from the group consisting of poly(vinyl chloride), polyurethane, and combinations thereof; and wherein the potentiometric ion selective electrode is more selective to $Mg^{2+}$ than to $Ca^{2+}$, and wherein the potentiometric ion selective electrode is substantially stable upon exposure to a reagent comprising a poly(ethylene oxide) surfactant; and
at least one reagent comprising a poly(ethylene oxide) surfactant, wherein the poly(ethylene oxide) surfactant is represented by the structure of Formula V, VI, or VII:

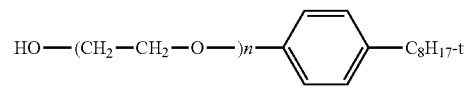

Formula V

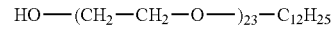

Formula VI

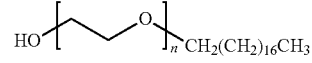

Formula VII wherein n in Formula V is in the range of from 9 to 10, and n in Formula VII is 100.

12. The kit of claim 11, wherein the at least one reagent comprising a poly(ethylene oxide) surfactant is one or more calibration reagents.

13. The kit of claim 12, further comprising at least one additional reagent comprising a poly(ethylene oxide) surfactant, wherein the at least one additional reagent is a wash reagent, a quality control reagent, and another calibration reagent.

14. The kit of claim 11, wherein the at least one reagent is one or more quality control reagents.

* * * * *